US012406562B2

United States Patent
Deshpande

(10) Patent No.: US 12,406,562 B2
(45) Date of Patent: Sep. 2, 2025

(54) IN-HOME EVENT INTERCOM AND NOTIFICATIONS

(71) Applicant: Apple Inc., Cupertino, CA (US)

(72) Inventor: Kshitij S. Deshpande, San Jose, CA (US)

(73) Assignee: Apple Inc., Cupertino, CA (US)

( * ) Notice: Subject to any disclaimer, the term of this patent is extended or adjusted under 35 U.S.C. 154(b) by 226 days.

(21) Appl. No.: 18/142,451

(22) Filed: May 2, 2023

(65) Prior Publication Data

US 2023/0360507 A1  Nov. 9, 2023

Related U.S. Application Data

(60) Provisional application No. 63/337,952, filed on May 3, 2022.

(51) Int. Cl.
*H04M 9/00* (2006.01)
*G08B 21/04* (2006.01)
*G16H 40/67* (2018.01)
*H04W 68/10* (2009.01)

(52) U.S. Cl.
CPC ..... *G08B 21/0446* (2013.01); *G08B 21/0476* (2013.01); *G16H 40/67* (2018.01); *H04M 9/00* (2013.01); *H04M 9/001* (2013.01); *H04W 68/10* (2013.01)

(58) Field of Classification Search
CPC .......... H04M 9/001; H04M 9/00; H04M 9/08; H04W 4/029; H04W 4/203; H04W 4/33; H04W 68/00; H04W 68/10; H04W 68/12
See application file for complete search history.

(56) References Cited

U.S. PATENT DOCUMENTS

| | | | |
|---|---|---|---|
| 2013/0211291 A1* | 8/2013 | Tran ..... | G08B 25/016 600/595 |
| 2014/0188516 A1 | 7/2014 | Kamen et al. | |
| 2016/0226542 A1 | 8/2016 | Tran et al. | |
| 2018/0310159 A1* | 10/2018 | Katz ..... | H04M 3/42161 |
| 2021/0133886 A1* | 5/2021 | Williams ..... | G06Q 40/08 |

OTHER PUBLICATIONS

International Patent Application No. PCT/US2023/020907, "International Search Report and the Written Opinion", Jul. 13, 2023, 12 pages.
International Patent Application No. PCT/US2023/020907, "International Preliminary Report on Patentability", Nov. 14, 2024, 9 pages.

* cited by examiner

*Primary Examiner* — Benyam Haile
(74) *Attorney, Agent, or Firm* — Kilpatrick Townsend & Stockton LLP

(57) ABSTRACT

Techniques are disclosed for in-home health intercom and notification. In one example, a first device receives a message comprising a description of an event of a first person in an environment from a first user device using a first transmission protocol. The first device detects that the message is an event message. The first device transmits the event message to the second computing device in the environment using a second transmission protocol, where the first device and the second device are in operable communication using a local area network. The first device receives, using the second transmission protocol, a response from the second device that the second computing device has transmitted the event message to a second user device.

20 Claims, 14 Drawing Sheets

IN-HOME EVENT INTERCOM AND NOTIFICATIONS

CROSS-REFERENCE TO RELATED APPLICATIONS

This application is claims priority under 35 U.S.C. § 119(e) to U.S. Provisional Application No. 63/337,952, filed on May 3, 2022, the contents of which is herein incorporated by reference.

BACKGROUND

Modern electronic devices are seamlessly integrated into our surroundings, such as in a home environment or an office environment. These electronic devices are becoming increasingly popular for users accessing a range of healthcare-based applications. Users can connect to the Internet via an electronic device in their home or office and access healthcare-based applications via their mobile phones, tablet computers, home entertainment systems, and the like.

BRIEF SUMMARY

In some implementations, a first computing device receives an event message (e.g., a health event message) from a first user device via a short-range transmission protocol. The message includes a description of an event (e.g., a health event) experienced by a first person in a home environment. The first computing device can be in operable communication with a second computing device via a smart home platform that manages the home environment. The first computing device transmits the message to the second computing device via an internet-based transmission protocol. The second computing device can detect a second person in the home environment that can render assistance to the first person. The first device receives, via the internet-based transmission protocol, a response from the second device that the second computing device has detected the second person and has transmitted the message to a second user device associated with the second person.

In some implementations, the first computing device transmits the message to multiple computing devices, including the second computing device, throughout the environment. Along with the message, the first computing device transmits instructions to each other computing device in the home environment to determine whether another person in the home environment can be detected. Each of the multiple computing devices can determine whether they are in proximity to a user device associated with a person. Upon detection of the device, each of the multiple computing devices can determine the likelihood that the person associated with the user device is still in proximity. Each of the multiple computing devices can then transmit a response back to the first computing device as to whether they have detected a person that can render assistance.

In some implementations, the first computing device can initiate a virtual assistant in response to receiving the message. The virtual assistant can be integrated with the first computing device. The virtual assistant can ask the first person whether they want assistance. The virtual assistant can receive and record a response from the first person. The virtual assistant can further analyze the response to determine whether the first person wants assistance. The first computing device can transmit the message to the second computing device based on whether the first person wants assistance.

Implementations offer at least the following advantages. The first user device that detects the event and transmits the message to the first computing device is likely a battery-powered device. By transmitting the message via a short-range transmission protocol, the first user device can conserve battery power. The conserved battery power can be used to power an alert signal, such as flashing lights or sounds, to help people find the first person. The first computing device can communicate with other devices in the home environment to find someone who can render assistance to the first person. By finding someone in the home environment, the in-home health intercom and notification system reduces the response time for providing aid to the first person.

DETAILED DESCRIPTION

Figure 1:
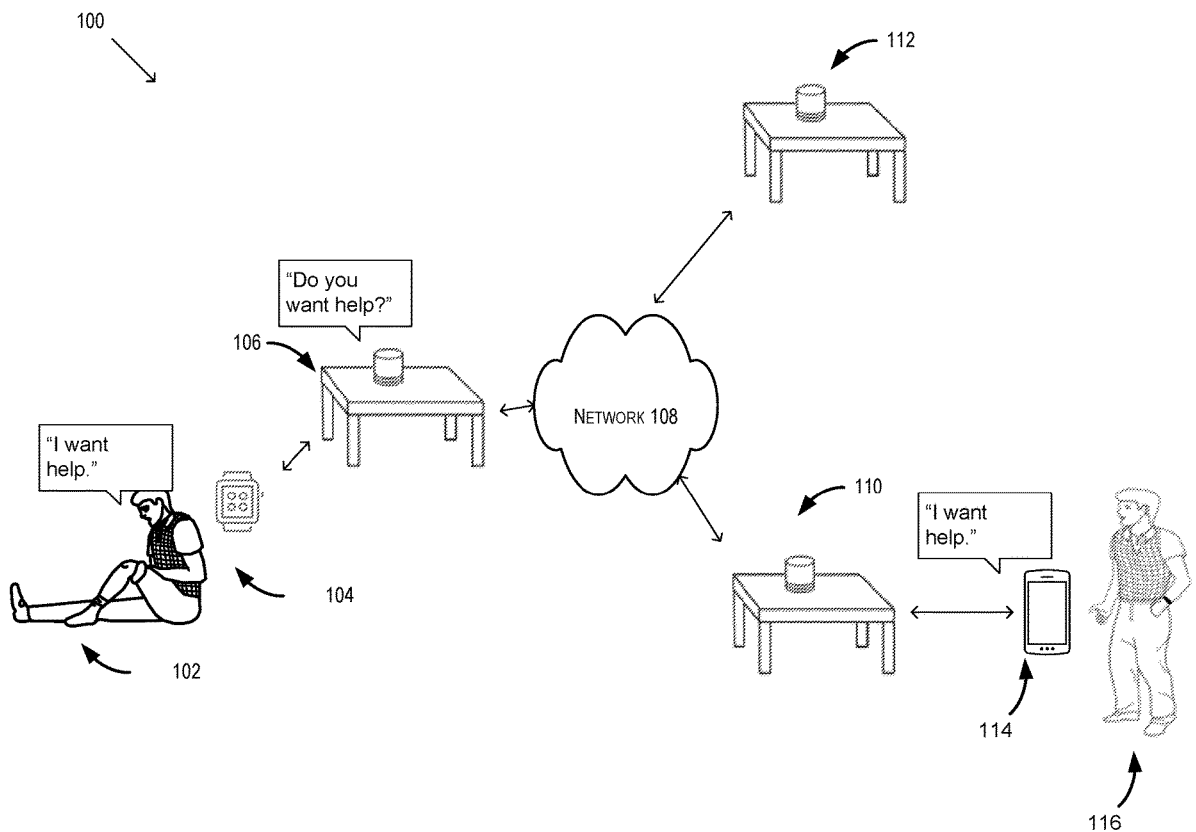
FIG. 1 is a diagram of an in-home health intercom and notification system, according to one or more embodiments.

In the following description, various examples will be described. For the purposes of explanation, specific configurations and details are set forth to provide a thorough understanding of the examples. However, it will also be apparent to one skilled in the art that the examples may be practiced without the specific details. Furthermore, well-known features may be omitted or simplified in order not to obscure the example being described.

Computing devices are integrated throughout the modern home and office environments. These computing devices can execute software applications that improve the daily lives of users and help maintain their health. For example, wearable devices can include biometric scanners for monitoring our physiological characteristics, and fall detection systems can detect whether a user has fallen. In some instances, wearable devices can further alert a health care provider or emergency medical services if an adverse event (e.g., an adverse health event) is detected, such as an irregular heartbeat or a fall. One issue is whether the person wants automatic communication with emergency medical services or a health care provider. In many instances, a person may simply recover on their own. For example, not every fall requires emergency medical services to respond. Another issue is the conservation of power. In many instances, these automatic alerts are issued through Wi-Fi or cellular networks that draw more power than short-range transmission protocols. A person who wants assistance may need their device power to last as long as assistance can arrive. Transmitting messages through more power-dependent transmission protocols can waste valuable battery life.

Embodiments described herein address the above-described issues by leveraging device connectivity to enable a computing device to detect whether a person wants assistance and relay a message to another person in the same area. A user device can detect that a first person in a home environment wants assistance. For example, the user device can be equipped with positional sensors that detect that the first person has fallen in a particular room/area (e.g., the kitchen of a home). The user device can generate an event message (e.g., a health event message) and transmit that message to another device in the home. The event message can include an identifier that indicates that the message is an event message. The message can be transmitted via short-range wireless technology to conserve power. A first resident device can receive the message and then transmit the message to other resident devices throughout the location to search for someone who can provide assistance. The resident devices can be connected to external power and therefore communicate via more power-dependent transmission protocols (Wi-Fi and cellular). The more power-dependent transmission protocols have a greater signal range which improves the probability of finding someone in the home that can provide assistance.

In some embodiments, each resident device in a home environment may be configured to perform embodiments of the present disclosure. In some embodiments, one or more resident devices may perform operations to synchronize (e.g., and/or coordinate operations) with each other. For example, a particular resident device of the environment may be selected among other resident devices to perform one or more of the embodiments described herein. In this example, other resident devices (e.g., in different rooms of the environment) may route messages to selected resident devices for performing these operations (e.g., identifying recipient devices and/or relaying the announcement to other devices of the home environment). Each resident device is generally configured for a specific location in the environment. For example, a smart speaker can be specific to a kitchen, whereas another smart speaker can be specific to a bedroom. Each resident device is generally connected to a wall socket and therefore be configured to not be moved often, as opposed to a smartwatch or a smartphone that moves about with a user. Additionally, each resident device that receives the message from the first resident device can locally determine whether they are near someone that can provide aid. In some embodiments, the determination can be based on a confidence score that a person is near the resident device. In the instance that a resident device determines that it is near someone, it can transmit the message to that person's user device (e.g., mobile device, smartwatch). This person can receive the message and provide assistance to the first person experiencing the event.

FIG. 1 is a diagram of an in-home health intercom and notification system, according to one or more embodiments. The in-home health intercom and notification system 100 can be implemented in an environment such as a home environment or an office environment, or at any location with a network of connected devices such as a rental property, park, or other public place. Each environment may correspond to a defined (e.g., limited) area and/or structure (e.g., dwelling unit). A home environment is described with more particularity with reference to FIG. 2. The in-home health intercom and notification system 100 enables a resident device to determine that someone in an environment is experiencing an event, to find another person in the same environment, and send a message to that other person.

In the event that more than one person is in the environment, the resident device can send the message to each person in the environment. For example, if two or more people are in the environment, the resident device can send the message to each of those people's devices. This feature is described in more particularity with respect to FIGS. 4 and 14.

As illustrated, a first person 102 can experience an event, such as a heart attack or a fall inside the environment. A device, such as a first user device 104, can detect that the first person 102 has experienced an event and may want assistance. For example, the first user device 104 can be a smartwatch with position-detecting hardware, other sensors, and accompanying software. The smartwatch can include sensors that detect, for example, the falling motion of the first person 102. For example, the smartwatch can also include sensors that detect the first person's heart rate, blood pressure, or other biometric data. The smartwatch can further include software that translates the sensor data to determine whether the first person 102 has experienced an event.

In other embodiments, the first user device 104 can be an image-capturing device with image recognition software. The image-capturing device can capture images as time-series data of the first person 102. The image-capturing device can access software that implements a neural network (e.g., a gated recurrent unit (GRU) network or a long short-term memory (LTSM) network) that analyzes the images and determines whether the first person 102 has experienced an event.

The first user device 104 can generate an event message (e.g., a health event message) in response to determining that the first person 102 has experienced or is experiencing an event. The message can include an identity of the first person 102. In many instances, the first user device 104 is associated with a user account. For example, the first user device 104 includes security features for the first user device's operating system. The security features can include an identity of the first person 102. In other instances, the first person's identity can be confirmed through other services associated with the first person 102 and the first user device 104. The message can further include an alert that the first person 102 may want assistance. The message can further include a location of the first user device 104. For example, the first user device 104 can include a location service to determine the location. The first user device 104 can determine its location using the service and include this location in the message. The message can further include an identifier indicating that the message is an event message.

The first user device 104 can locate the nearest resident device. In many instances, the first user device 104 is connected to resident devices via a local network. In other instances, the first user device 104 can be connected to resident devices via a smart home platform (e.g., Apple's HomeKit®). In instances where the first user device 104 is connected to resident devices via a local area network (LAN), the first user device 104 can discover other devices connected to the network via the LAN. For example, as the first user device 104 is moved about the environment, it can discover other devices as it passes by the devices. In instances that the first user device 104 is connected to resident devices through a smart home platform, the first user device 104 can discover other devices via the platform. In each instance that the first user device 104 discovers another computing device, the first user device 104 can store the discovery in its local memory.

In response to detecting an event, the first user device 104 can scan its local memory and determine the last discovered device. For example, the first user device 104 can store each discovered device's identifier and network address (e.g., media access control (MAC) address) in memory. The first user device can then compare time stamps associated with discovering these devices to determine the last discovered device. The last discovered device is likely to be the closest device to the first user device 104. Therefore, the last discovered device can likely be reached via a short-range transmission protocol.

As illustrated, the last discovered device in the environment is the first resident device 106. The first user device 104 can transmit the message to the first resident device 106 via a first transmission protocol, which can be a short-range transmission protocol, for example, a wireless technology such as Bluetooth, Zigbee, or the like. If a person wants assistance, preserving the battery life of the person's device can provide the person more time to reach and communicate with another person. A short-range transmission protocol draws less power from a device than other transmission protocols, such as Wi-Fi and cellular. Therefore, the first user device 10 conserves battery life by communicating with the first resident device 106 via the first transmission protocol.

The first resident device 106 can receive the message from the first user device 104. In some instances, the first resident device 106 is integrated with a virtual assistant (e.g., Siri®). For example, the first resident device 106 is a smart speaker with an integrated virtual assistant. In these instances, the first resident device 106 can transmit computer-readable instructions to the virtual assistant to direct the assistant to verify whether the first person 102 wants assistance. The virtual assistant can inquire whether the first person 102 wants assistance. As illustrated, the virtual assistant can use the first resident device's speakers to ask the person, "Do you want help?" The virtual assistant can further record a response from the first person 102. As illustrated, the first person 102 says, "I want help," in response to the virtual assistant's question. The first resident device 106 can record the response, for example, through microphones integrated with the smart speaker. In other instances, the first resident device 106 can include other recording capability, for example, image-capturing hardware. In these instances, the first resident device can capture an image or set of images of the response.

Based on the response, the first resident device 106 can determine whether the first person 102 wants assistance. For example, the virtual assistant can have access to natural language processing (NLP) capability, such as an NLP service. The virtual assistant can also have access to image processing capability, such as a neural network. The virtual assistant can transmit its determination to the first resident device 106. If the virtual assistant determines that the first person 102 does not want assistance, the first resident device 106 can cease processing the message. If the first resident determines that the first person 102 wants assistance, it can continue to process the message. In some events, the first person 102 can be incapacitated or otherwise unable to respond to a query from the virtual assistant. Therefore, the virtual assistant can start a counter or countdown timer from the moment of asking the question. If the first person 102 does not respond within a threshold time, the virtual assistant can determine that the first person wants assistance.

The first resident device 106 can be connected via a network 108 to a second resident device 110 and a third resident device 112. Each of the second resident device 110 and the third resident device 112 can be, for example, a smart speaker. The network 108 can be a local network communicating over a second transmission protocol, such as Wi-Fi or cellular. The first resident device 106 can transmit the message to each other resident device in the environment via the second transmission protocol. In some embodiments, the first resident device 106 can select the second transmission protocol based on receiving a message. For example, the first resident device 106 can include logic that causes the first resident device 106 to use the second transmission protocol based on receiving the message. In instances that the virtual assistant obtains a recording of the first person 102, the first resident device can further append the message to include the recording.

It is customary for resident devices in an environment to be connected to power via an outlet rather than battery power. Therefore, the power consideration for the resident devices is different from for the first user device 104. Therefore, the first resident device 106 can transmit the message to the second resident device 110 and the third resident device 112 via a second transmission protocol, such as Wi-Fi or cellular. It should be appreciated that although only a first resident device 106, a second resident device 110, and a third resident device 112 are shown, the environment can include as many resident devices as desired, or as few as one.

Each of the second resident device 110 and the third resident device 112 can determine whether they can detect a person. Each of the second resident device 110 and the third resident device 112 can determine whether they can detect a user device that is associated with a person's account. In some embodiments, the second resident device 110 and the third resident device 112 can further make the determination, based on a confidence score, whether a second person associated with the user device is present.

The confidence score can be based on various factors, and each resident device can calculate a confidence score based on sensory inputs. The sensory inputs can be, for example, accelerometer-based data, gyroscope-based data, touch-based sensor data, audio data, device charging information, and application data. The sensory inputs can be collected locally by the resident device, or one or more other devices can collect input data and transmit the input data to the resident device. For example, the other device can be any type of device that is able to perform sensing capabilities, such as a microphone, a motion-sensing device, a position-sensing device, a location-sensing device, an image-capturing device, or a temperature-sensing device that is paired with the resident device.

Each resident device can calculate a confidence score that describes the likelihood that a person is present. For example, the resident device can be a tablet, and a person can be engaging with the tablet (e.g., using a word processing application, streaming video or audio, etc.). The resident device can calculate the confidence score based on the person's level of engagement with the tablet (e.g., with the word processing or other application). For example, if the person is actively typing via the word processing application, the resident device can calculate a confidence score that suggests the person is present. If, however, the person has stopped typing, the resident device can look to the time elapsed from the last instance of typing. If the time elapsed is greater than the threshold time, the confidence score can suggest that the person has moved away from the resident device.

The resident device can evaluate multiple factors when calculating the confidence score. These factors can include historical data associated with an application. For example, in addition to the length of the elapsed time, the resident device can access historical data regarding the average length of time that the person pauses while typing via the word processing application. In this example, the resident device can calculate the confidence score based on the elapsed time and the average length of time. The resident device can further engage a set of heuristics for determining whether to weigh one factor more than another factor.

As illustrated, the second resident device 110 can detect the second user device 114 and determine that a second person 116 is present. The second resident device 110 can further transmit the message to the second user device 114. The second user device 114 can display the message for the second person 116. The second resident device 110 can transmit a message back to the first resident device that it has detected the second person 116 and transmitted the message.

As described above, in some embodiments, the message can include a recording of the first person 102. For example, the second user device 114 can play the recording, "I want help," for the second person 116. The message can further relay the identity and location of the first person 102 to the second person 116. The second person 116 can then go to the location in the environment where the first person 102 is located to render aid.

Figure 2:
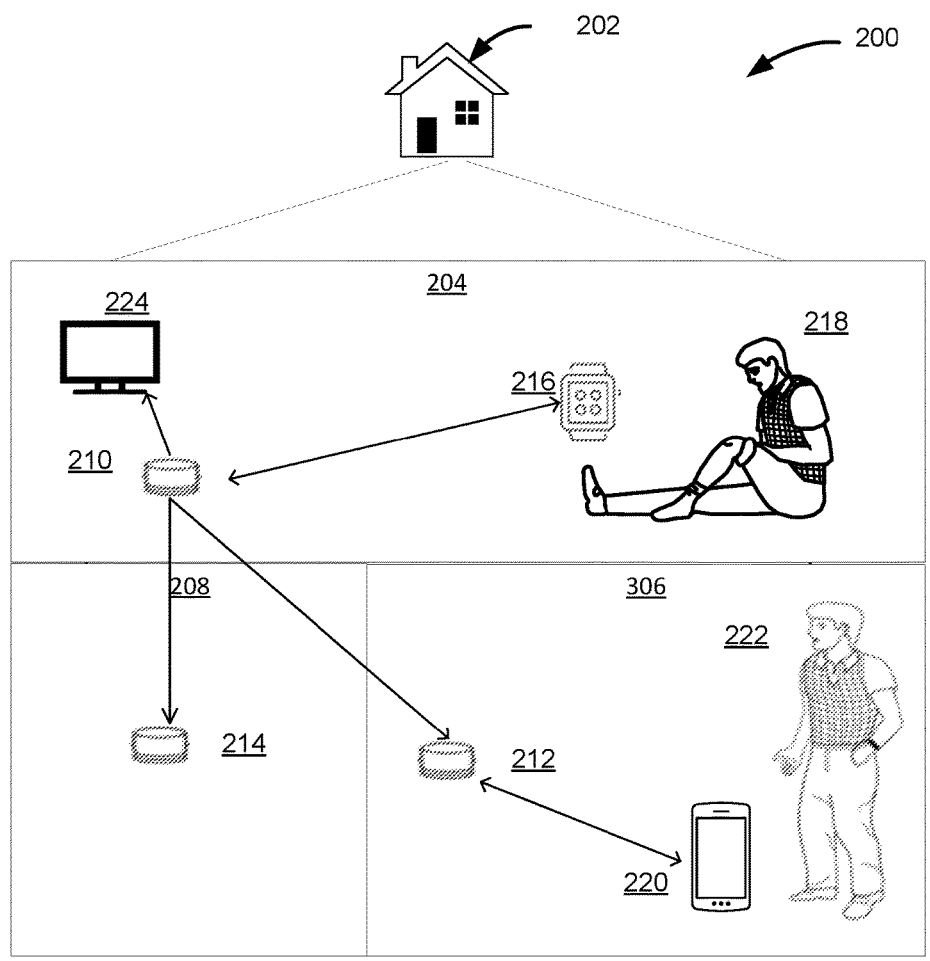
FIG. 2 is a diagram of an in-home intercom and notification system in a home environment, according to one or more embodiments.

FIG. 2 is a diagram of an in-home intercom and notification system in a home environment, according to one or more embodiments. In some embodiments, the in-home health intercom and notification system 100 of FIG. 1 can be implemented in the home environment 202. Turning to the elements of the home environment 202 in further detail, multiple elements are depicted. The home environment 202 can contain multiple rooms. As illustrated, the home environment 202 includes a first room 204, a second room 206, and a third room 208. The first room 204 can be, for example, an upstairs bedroom. The second room 206 can be, for example, a kitchen, and the third room 208 can be, for example, a family room. As illustrated, a first resident device 210 (e.g., a smart speaker) can be positioned within the first room 204 and be associated with the bedroom. For example, the first resident device 210 can be associated with an account holder that has the first room 204 in the home environment 202. Similarly, a second resident device 212 can be positioned within the second room 206 and associated with the kitchen. A third resident device 214 can be positioned within the third room 208 and associated with the family room. In some embodiments, one or more associations (e.g., between a resident device and a particular room) can be stored by one or more resident devices of the home environment 202.

The devices located in the home environment 202 can be managed by a smart home platform. The smart home platform can be software that enables authorized users to coordinate and control home automation accessories, regardless of the vendor, from a graphical user interface (GUI). Each of the first resident device 210, the second resident device 212, and the third resident device 214 can be associated with the home environment 202. As illustrated, each resident device is located within a home. However, it should be appreciated that one or more resident devices can be located outside of the physical home, such as in a detached garage, detached mother-in-law suite, or shed. Each of the resident devices can be associated with user accounts that are registered on the smart home platform. The user accounts can be authorized users directly associated with the home environment 202. For example, the authorized users can include a mother and a father living in the home. The user accounts can further be associated with authorized user users indirectly associated with the home environment 202. For example, a user account can be associated with a babysitter, a house sitter, or a long-term guest.

In addition to these resident devices, the home environment 202 can be associated with a number of accessory devices such as smart lights, door locks, and appliances. An authorized user can use their smartphone to access a smart home GUI to access the smart home platform. The user can further manipulate the GUI to control the accessories, such as the smart lights. The home environment 202 can be a home that incorporates the resident devices and the accessory devices; and is managed by the smart home platform.

Also located within the home environment 202 can be a first user device 216 (e.g., a smartwatch) in the first room 204, and associated with a first person 218. A second user device 220 (e.g., a mobile phone) can be located within the second room 206 and can be associated with a second person 222. One or both of the user devices can be associated with user accounts associated with the home environment 202. For example, the first user device 216 can be associated with a grandfather's user account, which is registered on the smart home platform. In other instances, one or both of the user devices can be devices that are not registered on the smart home platform. For example, the second user device 220 can be associated with a handyman performing repairs in the home.

As illustrated in FIG. 2, the proximity of the first user device 216 to the first resident device 210 may be greater than the proximity of the first user device 216 to the second resident device 212 or the third resident device 214. It should be appreciated that although a home environment 202 is depicted in FIG. 2, a similar layout could be envisioned in an office environment.

In some embodiments, an event message (e.g., a health event message) can be received or transmitted by any one of the devices depicted. In some embodiments, a sending device may receive instructions corresponding to a selection of a transmission protocol for transmitting the message. In some embodiments, the sending device may also (or alternatively) receive instructions corresponding to a selection of one or more devices (e.g., resident devices) for transmitting the message. As described herein, any one of the resident devices (e.g., first resident device 210, second resident device 212, and third resident device 214) may be used to transmit an event message to other devices and/or locations within the home environment 202. Accordingly, although a resident device may be primarily described in embodiments herein as transmitting announcements to other devices, embodiments should not be construed to be so limiting (e.g., a suitable user device and/or server device may also perform the operations of embodiments described herein).

In some embodiments, a sending device (e.g., a resident device, or suitable user device) may be configured to transmit a health care event to a particular device (e.g., a particular user device and/or a particular resident device) based on a detected proximity between one or more devices. In some embodiments, one or more devices associated with the home environment 202 may transmit location information (e.g., GPS coordinates, velocity and/or acceleration information, etc.) to a resident device of the home environment. In some embodiments, any suitable real-time location service (RTLS) may be used to determine location information (e.g., location data) of a device. Based on the location information determined with respect to each device, the resident device may determine a location of each device and/or a relative proximity between devices. As illustrated further in representative scenarios described below, this location and/or proximity information may be used to select a particular one or more devices for receiving the health care event message.

Consider a scenario in which the first person 218 experiences an event (e.g., falling down, accelerated heartbeat) that is detected by a sensor of the first user device 216. The first user device 216 can determine which other device it detected last. For example, each other device can be configured to periodically advertise its device identifiers across a transmission protocol, such as a Wi-Fi network, and the first user device 216 can search its memory to determine which device identifier was received last. In another example, the first user device 216 can transmit a signal to discover another device via a short-range transmission protocol, such as Bluetooth or Zigbee. The first user device 216 can determine the distance between itself and another device based on the strength of the response signal from the other device.

As illustrated, the first user device 216 can discover the first resident device 210. The first resident device 210 can be in the first room 204, as can the first user device 216 and the first person 218. As illustrated, the first resident device 210 has the greatest proximity to the first user device 216. The first resident device 210 can initiate a session with the first user device 216 via a first transmission protocol, such as a short-range transmission protocol. The first resident device 210 and the first user device 216 can actively form a connection, and each can enter a connection state. The connection does not require an authentication process in which the first person 218 needs to authorize the connection. As described above, the use of the short-range transmission protocol is to conserve the battery life of the first user device 216.

The first user device 216 can retrieve a location using a location service. The first user device 216 can generate a message that can include a location of the first user device 216, an identity of an account holder associated with the first user device 216, and computer-readable instructions for the first resident device 210.

The first resident device 210 can receive the message from the first user device 216 via the short-range transmission protocol. In some embodiments, the first resident device 210 can initialize a virtual assistant in response to receiving the message. The virtual assistant can be a software agent executing on the first resident device 210 and integrated with the smart home platform. The virtual assistant can respond and perform tasks based on commands or questions. The virtual assistant can inquire whether the first person 218 wants assistance. The virtual assistant can communicate with the first person 218 via the first resident device 210. For example, if the first resident device 210 is a smart speaker, the virtual assistant can speak to the first person 218 through the speaker. The virtual assistant can further record a response via the software and hardware such as a microphone and/or an image-capturing device of the first resident device 210.

The first resident device 210 can transmit the message to each other resident device in the home environment 202 via a second transmission protocol, such as a Wi-Fi. Each resident device in the home environment 202 is connected to a local network such as a Wi-Fi network. Each resident device further includes identifying information such as address and names for each other resident device in memory. As illustrated, the first resident device 210 can identify each other device and transmit the message to the second resident device 212 and the third resident device 214 via the second transmission protocol. In embodiments in which the first resident device 210 initializes a virtual assistant, the first resident device 210 transmits the message with a recording from the first person 218.

Resident devices such as smart speakers are likely to draw power via a wall socket rather than a battery. Therefore, the power consumption concerns in choosing to use the short-range transmission protocol or an internet-based transmission protocol can be more pronounced for the first user device 216, which is likely powered by batteries. Additionally, a message transmitted via an internet-based transmission can have a greater range than a message transmitted via a short-range transmission protocol. Therefore, the first resident device 210 can communicate with the second resident device 212 and the third resident device 214 over the second transmission protocol. By transmitting the message to each resident device over the second transmission protocol, the first resident device 210 increases the probability that the message reaches someone who can render assistance.

Each of the second resident device 212 and the third resident device 214 can receive the message from the first resident device 210 via the second transmission protocol. As illustrated, the first resident device 210 transmits the message from the first room 204 to a second resident device 212 in the second room 206, and a third resident device 214 in the third room 208 of the home environment 202. The message can include computer-readable instructions to determine whether either resident device can detect a person.

Each of the second resident device 212 and the third resident device 214 can determine whether it can detect a person in their respective room. In some embodiments, if the second resident device 212 or the third resident device 214 detect a second user device, it can be presumed that a second person is present with the device. As described above, in some other embodiments, determining that a person is in the environment is based on a confidence score that a person is present. Each of the second resident device 212 and the third resident device 214 can perform various techniques to detect a user device. For example, the second resident device 212 and the third resident device 214 can search their memory to determine whether a user device was discovered. In another example, each other device can transmit a signal to discover another device via a short-range transmission protocol, such as Bluetooth or Zigbee. If the second resident device 212 or the third resident device 214 detect another user device, they can send the event message to the detected user device.

The second resident device 212 and the third resident device 214 can then make the determination, based on a confidence score, whether a person is present. As described above, the determination can be based on various factors. For example, a person pushes a volume button on a smart speaker within a threshold period of time. Another example can be receiving an audio signal within a threshold period of time. Another example can be detecting a device associated with a person within a threshold period of time. For instance, detecting a smartphone or a smartwatch registered to a user. If, based on the confidence score, a person is present, the resident device can transmit a message to the first resident device 210, that a person is present.

As illustrated, no person or user device is located in the third room 208 with the third resident device 214. As illustrated, the second resident device 212 is located in the second room with the second person 222. The second resident device 212 can detect the second user device 220 and determine whether a person is present. The second resident device 212 can transmit a message back to the first resident device 210 that it has detected a person.

The second resident device 212 can transmit the message to the second user device 220. The message can be presented on the second user device 220 in a manner to capture the second person's attention. For example, if the second user device 220 is a smartwatch or a smartphone, the message can be presented as a widget on a display. The widget can be an extension of an application executing on the second user device 220. For example, the widget can be an extension of an SMS application or a smart home platform application. The widget can further occupy a larger space on a device display than a standard application icon. In some embodiments, the message includes a recording of the first person 218. For example, as illustrated in FIG. 1, the message included the recording, "I want help." The second user device 220 can include a prompt via an icon that allows the second person 222 to listen to the recording. The aspects of the message on the second user device 220 are described with more particularity with respect to FIG. 4. Upon receiving the message, the second person 222 can determine an identity of the first person 218, determine where the first person 218 is in the home environment 202, and receive a recording of the first person 218. The second person 222 can then go find and render assistance to the first person 218.

In some instances, the first resident device 210 does not receive any response from any other resident device in the home environment 202. The first resident device 210 can, for example, include a time tracking software that monitors the time elapsed after receiving the message from the first user device 216. In the event that a threshold time has elapsed after receiving the message from the first user device 216, the first resident device 210 can transmit a message to emergency services. For example, the first resident device 210 can transmit a message to a dedicated emergency services address via the internet.

The first resident device 210 can further detect one or more individuals that enter the environment. The individuals can be, for example, law enforcement officers, emergency medical technicians, ambulance drivers, or neighbors. The first resident device 210 can detect the individuals using a variety of techniques, such as device detection, motion sensing, audio sensing, and image sensing. The first resident device 210 can employ these techniques individually or in combination. For example, the first resident device 210 can be connected to a network, such as a local area network (LAN). In the event that an individual enters the environment with a device, the device can connect with the network. Furthermore, the connection, including a device identifier, can be broadcast to other devices in the network. In response to receiving the broadcast, the first resident device 210 can check its memory to determine if it has detected the device identifier before. Based on the contact with emergency services, the first resident device can determine that the individual has entered the environment in response to the event. In another example, the first resident device 210 can employ motion sensing and detect motion within the environment. For example, the first resident device can detect a door opening, a window opening, or a person moving about the environment.

In yet another example, the first resident device 210 can include hardware and software for enabling sensing capability, such as audio or visual sensing capability. The first resident device 210 can record its surroundings using the sensing capability. For example, in response to transmitting the message to emergency services, the first resident device can begin an audio and/or visual recording. The first resident device 210 can further analyze or transmit to a service for analysis of the recording to detection of an individual in the environment. The analysis can include determining that an individual has entered the environment and the nature of the individual. For example, if the first resident device 210 employs audio sensing capabilities, it can either determine that an individual has entered the environment based on the detection of various audio inputs, such as a sound of a door opening or a voice. The first resident device 210 can further determine the nature of the individual based on the audio inputs. For example, the first resident device 210 can directly or through a service employ natural language processing (NLP) techniques and determine the nature of the individual. For example, the NLP techniques can be used to detect identifying phrases, such as "law enforcement, entering the home," "emergency medical services, can you hear me," or "this is your neighbor, is everything fine?" The phrases can be mapped to the nature of an individual, such as "law enforcement officer, entering the home" can be mapped to law enforcement.

In yet even another example, if the first resident device 210 employs visual sensing capabilities, it can either determine that an individual has entered the environment based on the detection of various visual inputs, such as a door opening or an individual in the environment. It should be appreciated that the visual sensing capabilities can be an alternative to or in combination with audio sensing capabilities. The first resident device 210 can further determine the nature of the individual based on the visual inputs. For example, the first resident device 210 can directly or through a service employ image processing techniques and determine the nature of the individual. For example, the image processing techniques can be used to detect identifying objects, such as a law enforcement badge, a star of life badge, a face of a neighbor. The objects can be mapped to the nature of an individual, such as the star of life badge can be mapped to an emergency medical technician. It should be appreciated that in some instances, the first resident device 210 includes the hardware and software to offer sensing capabilities. In other instances, the first resident device 210 can receive sensor data from one or more other devices. For example, the first resident device 210 can receive sensor data from an audio and image-capturing device in the environment. As described above, the first resident device 210 can be connected to a network, as can other devices. If the first resident device 210 lacks one or more sensing capabilities, it can contact another device that is connected to the network and has those capabilities to begin recording. For example, after transmitting the message to emergency services, it can detect each other device connected to the network, message the other devices for a response describing sensing capabilities, and transmit a message to begin recording based on the responses.

In some instances, the home environment 202 can include a fourth resident device 224, capable of presenting audio or visual messages. The fourth resident device 224 can be, for example, a television or a laptop. As illustrated, the first room 204 includes a fourth resident device 224 in the form of a smart television. The fourth resident device 224 can be managed by the smart home platform that manages the home environment 202. The first resident device 210 can determine the nature of the first person's event. The first resident device 210 can further transmit instructions to present mitigation steps to the fourth resident device 224. For example, the first resident device 210 can receive information from the first user device 216 that the first person is choking. In response, the first resident device 210 can search for online resources for cardiopulmonary resuscitation (CPR) instructions. The first resident device 210 can further transmit computer-readable instructions directing the fourth resident device 224 to access the online resource to display the cardiopulmonary resuscitation (CPR) instructions. In some instances, the first resident device 210 can present mitigation steps in the event that there is no fourth resident device 224.

The first resident device 210 can further transmit a message to the first user device 216 that the second resident device 212 detected the second person 222. In response, the first user device 216 can present an alert signal. The alert signal can be any signal to draw attention to the first user device 216, and consequently the first person 218. For example, if the first user device 216 is a smartwatch or a smartphone, the device can present an auditory noise, such as a siren or beep. The first user device 216 can also present a visual effect, such as a strobe light effect or other light-based effect.

Figure 3:
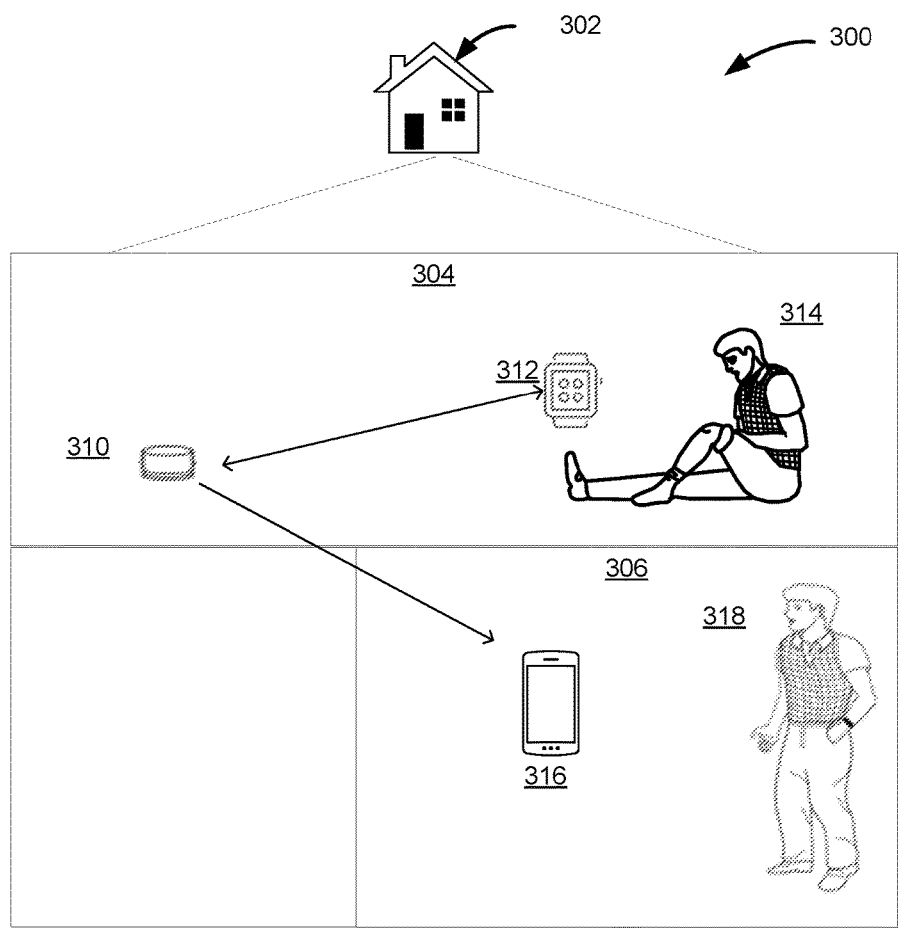
FIG. 3 is a diagram of an in-home intercom and notification system in a home environment, according to one or more embodiments.

It should be appreciated that the functionality described above can be performed using a single resident device, rather than multiple resident devices. For example, FIG. 3 is a diagram of an in-home intercom and notification system in a home environment, according to one or more embodiments. In some embodiments, the in-home health intercom and notification system 100 of FIG. 1 can be implemented in the home environment 302. Turning to the elements of the home environment 302 in further detail, multiple elements are depicted. The home environment 302 can contain multiple rooms. As illustrated, the home environment 302 includes a first room 304 and a second room 306. The first room 304 can be, for example, an upstairs bedroom. The second room 306 can be, for example, a kitchen. As illustrated, a resident device 310 (e.g., a smart speaker) can be positioned within the first room 304 and be associated with the bedroom. For example, the resident device 310 can be associated with an account holder that stays in the first room 304 in the home environment 302.

The resident device 310 can be managed by a smart home platform. The smart home platform can be software that enables authorized users to coordinate and control home automation accessories, regardless of the vendor, from a graphical user interface (GUI).

Also located within the home environment 302 can be a first user device 312 (e.g., a smartwatch) in the first room 304, and associated with a first person 314. A second user device 316 (e.g., a mobile phone) can be located within the second room 306 and can be associated with a second person 318.

A first person 314 experiences an event (e.g., falling down, accelerated heartbeat, etc.) that is detected by a sensor associated with the first user device 312. The first user device 312 can determine which other device (e.g., of a plurality of different other devices nearby or with which the first user device 312 recently communicated) it detected last. For example, each other device (e.g., the resident device 310, the second user device 316, or the like) can be configured to periodically advertise their device identifiers across a transmission protocol, such as a Wi-Fi network, and the first user device 312 can search local memory to determine which device identifier corresponding to another device was received last. In another example, the first user device 312 can transmit a signal to discover another device via a short-range transmission protocol, such as Bluetooth or Zigbee. The first user device 312 can determine the distance between itself and another device based on the strength of the response signal from the other device.

As illustrated, the first user device 312 can discover the resident device 310. The resident device 310 can be in the first room 304, as can the first user device 312 and the first person 314. The resident device 310 can initiate a session with the first user device 312 via a first transmission protocol, such as a short-range transmission protocol. The session may, in some examples, not require an authentication process in which the first person 314 needs to authorize the connection. As described above, one use of the short-range transmission protocol is to conserve the battery life of the first user device 312.

The first user device 312 can retrieve a location corresponding to its own location using a location service. The first user device 312 can generate a message, including the sensor data, that can include the location of the first user device 312, an identity of an account holder associated with the first user device 312, and computer-readable instructions for the resident device 310.

The resident device 310 can receive the message from the first user device 312 via the short-range transmission protocol. In some embodiments, the resident device 310 can initialize a virtual assistant in response to receiving the message. The virtual assistant can inquire whether the first person 314 wants assistance. For example, if the resident device 310 is a smart speaker, the virtual assistant can speak to the first person 314 through one or more speakers of the resident device 310. The virtual assistant can further record a response (e.g., using a microphone and/or an image-capturing device of the resident device 310).

The resident device 310 can determine whether it can detect a second user device in the home environment 302. If the resident device 310 can detect a second user device, it can be presumed that a second person is present. In some embodiments, determining that a second person may be based on a confidence score. The resident device 310 can perform various techniques to detect a user device (e.g., the second user device 316). For example, the resident device 310 can search its memory to determine whether a second user device was previously discovered.

The resident device 310 can transmit the message to the second user device 316. The message can be presented on the second user device 316 in a manner to capture the second person's attention. For example, if the second user device 316 is a smartwatch or a smartphone, the message can be presented as a widget or notification (e.g., a pop-up) on a display. In some cases, a widget can be an extension of an application executing on the second user device 316. For example, the widget can be an extension of an SMS application or a smart home platform application. The widget can further occupy a larger space on a device display than a standard application icon. Alternatively, the message may be presented as a pop-up notification, covering up other portions of the screen, including user interface elements with which a user was interacting. In some embodiments, the message includes a recording of the first person 314 or a recording of the first resident device's surrounding in instances that the first person 314 cannot communicate. In addition to the recording, the event message can further include an identity of the first person 314, a location of the first person 314 in the home environment 302. The second person 318 can then go find and render assistance to the first person 314.

In some instances, the resident device 310 may not detect any other user devices. The resident device 310 can, for example, include a time tracking software that monitors time elapsed after receiving the message from the first user device 312. If a threshold time has elapsed after receiving the message from the first user device 312, the resident device 310 can contact emergency medical services. Emergency medical services can include calling 911 or an emergency contact if an emergency contact has been provided.

The resident device 310 can further transmit a message to the first user device 312 that it has detected the second person 318. In response, the first user device 312 can present an alert signal. The alert signal can be any signal to draw attention to the first user device 312, and consequently the first person 314. For example, if the first user device 312 is a smartwatch or a smartphone, the device can present an auditory noise, such a siren or beep. The first user device 312 can also present a visual effect, such as a strobe light effect or other light-based effect.

Figure 4:
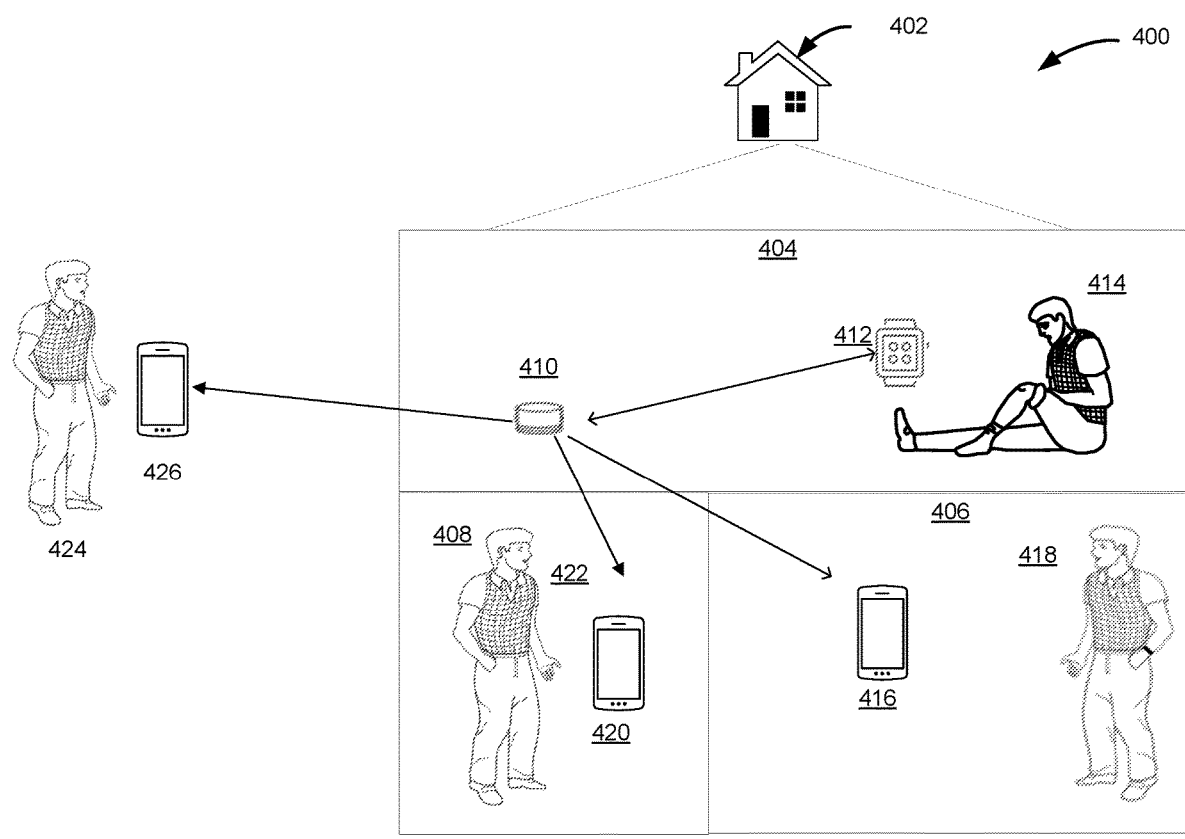
FIG. 4 is a diagram of an in-home intercom and notification system in a home environment, according to one or more embodiments.

FIG. 4 is a diagram of an in-home intercom and notification system in a home environment, according to one or more embodiments. Turning to the elements of the home environment 402 in further detail, multiple elements are depicted. The home environment 402 can contain multiple rooms. As illustrated, the home environment 402 includes a first room 404, a second room 406, and third room 408. The first room 404 can be, for example, an upstairs bedroom. The second room 406 can be, for example, a kitchen. The third room 408, can be, for example, a study. As illustrated, a resident device 410 (e.g., a smart speaker) can be positioned within the first room 404 and be associated with the bedroom. For example, the resident device 410 can be associated with an account holder that stays in the first room 404 in the home environment 402.

The resident device 410 can be managed by a smart home platform. The smart home platform can be software that enables authorized users to coordinate and control home automation accessories, regardless of the vendor, from a graphical user interface (GUI).

Also located within the home environment 402 can be a first user device 412 (e.g., a smartwatch) in the first room 404, and associated with a first person 414. A second user device 416 (e.g., a mobile phone) can be located within the second room 406 and can be associated with a second person 418. A third user device 420 (e.g., a mobile phone) can be located within the second room 406 and can be associated with a third person 422. Other variations of user devices in different rooms, zones, etc., are envisioned and the disclosure is not limited to the examples provided with respect to FIG. 4.

In some instances, the first person 414 can experience an event (e.g., falling down, accelerated heartbeat, etc.) that is detected by a sensor associated with the first user device 412. The first user device 412 can determine which other device(s) (e.g., of a plurality of different other devices nearby or with which the first user device 412 recently communicated) it can detect. For example, each other device (e.g., the resident device 410, the second user device 416, the third user device 420, or the like) can be configured to periodically advertise their device identifiers across a transmission protocol, such as a Wi-Fi network, and the first user device 412 can search local memory to determine which device identifier corresponding to another device was received last. In another example, the first user device 412 can transmit a signal to discover another device via a short-range transmission protocol, such as Bluetooth or Zigbee. The first user device 412 can determine the distance between itself and another device based on the strength of the response signal from the other device.

As indicated above, the residence device 410 can be managed by a smart home platform (e.g., Apple HomeKit). In some instances, a person (e.g., the first person 414, the second person 418, or the third person 422) with administrative privileges for the smart home platform may have added a fourth person 424 to the smart home platform. As illustrated, the fourth person 424 can be located outside of the home environment 402. In some examples, the fourth person 424 may be in a relationship with the first person 414 (e.g., martial or otherwise) and may have gone out for grocery shopping. The resident device 410 can be aware of the fourth person 424 as a result of being registered on the smart home application. The resident device 410 can be configured to communicate with a fourth user device 426 associated with the fourth person 424. As the fourth person 424 can be outside the home environment 402, the resident device 410 can be configured to communicate with the fourth user device 426 using a variety of transmission protocols, such as cellular, Wi-Fi, or Internet-based communication.

As illustrated, the first user device 412 can discover the resident device 410. The resident device 410 can be in the first room 404, as well as the first user device 412 and the first person 414. The resident device 410 can initiate a session with the first user device 412 via a first transmission protocol, such as a short-range transmission protocol. The session may, in some examples, not require an authentication process in which the first person 414 needs to authorize the connection. As described above, one use of the short-range transmission protocol is to conserve the battery life of the first user device 412.

The first user device 412 can retrieve a location corresponding to its own location using a location service. The first user device 412 can generate an event message, including the sensor data, that can include the location of the first user device 412, an identity of an account holder associated with the first user device 412, and computer-readable instructions for the resident device 410.

The resident device 410 can receive the event message from the first user device 412 via the short-range transmission protocol. In some embodiments, the resident device 410 can initialize a virtual assistant in response to receiving the message. The virtual assistant can inquire whether the first person 414 wants assistance. For example, if the resident device 410 is a smart speaker, the virtual assistant can speak to the first person 414 through one or more speakers of the resident device 410. The virtual assistant can further record a response (e.g., using a microphone and/or an image-capturing device of the resident device 410).

The resident device 410 can determine whether it can detect another user device in the home environment 402. If the resident device 410 detects another user device, it can be presumed that a person associated with the user device is present. In some embodiments, determining that another person is present in the home environment 402 may be based on a confidence score. The resident device 410 can perform various techniques to detect other user devices (e.g., the second user device 416 and the third user device 420). For example, the resident device 410 can search its memory to determine whether the other user device was previously discovered. The discovery of the other user devices can be based on a notification that the other user device has connected with a local network used by the resident device 410. In other instances, the resident device 410 can discover another user device in the home environment 402 based on a signal transmitted by the other device to the resident device 410.

The resident device 410 can further determine whether it can detect another user device based on the user device being associated with the smart home platform. As indicated above, a person can add one or more user accounts to a smart home platform. The smart home platform can receive users identification and user device information for each account associated with the smart home platform. For example, one person can add an account for the other spouse or sibling to their smart home platform. Consider a situation, in which person A has a residence with one or more devices controllable by a smart home application. Person A can add an account for person B to their smart home platform. Person B can be, for example a person that also lives in the home, or person B can also be, for example, a person that lives in another home. In any event, the smart home platform can be configured with each added person's information, identification, device identifier, contact information. The smart home platform can operate as an application on the resident device 410, and the resident device can communicate with the smart home platform to identify persons added to the smart home platform.

The resident device 410 can generate and transmit the event message to each identified device (e.g., second user device 416, third user device 40 and fourth user device 426). The resident device 410 can also send the identity of each detected user device along with the event message. Therefore, the event message can include a recording of the first person 414 or a recording of the resident device's surrounding in instances that the first person 414 cannot communicate. The event message can further include a location of the source of the message. For example, if the first person is located in the home environment 402, the message can include an indication that the message originated from the home. In addition to the recording and location, the resident device 410 can include an identity of the first person 414 and/or a location of the first person 414 in the home environment 402. The resident device 410 can also send an identity of the other detected devices. For example, the resident device 410 can send a transmission to the second user device 416 that includes the event message and an indication that the resident device 410 transmitted the event message to the second user device 416, the third user device 420 and the fourth user device 426. The event message and the identities of the other uses devices can be sent as a single message or a set of messages.

The resident device 410 can further transmit a message that it has detected another person to the first user device 412. In response to receiving the message from the resident device 410, the first user device 412 can present an alert signal. The alert signal can be any signal to draw attention to the first user device 412, and consequently the first person 414. For example, if the first user device 412 is a smartwatch or a smartphone, the device can present an auditory noise, such as a siren or beep. The first user device 412 can also present a visual effect, such as a strobe light effect or other light-based effect.

Figure 5:
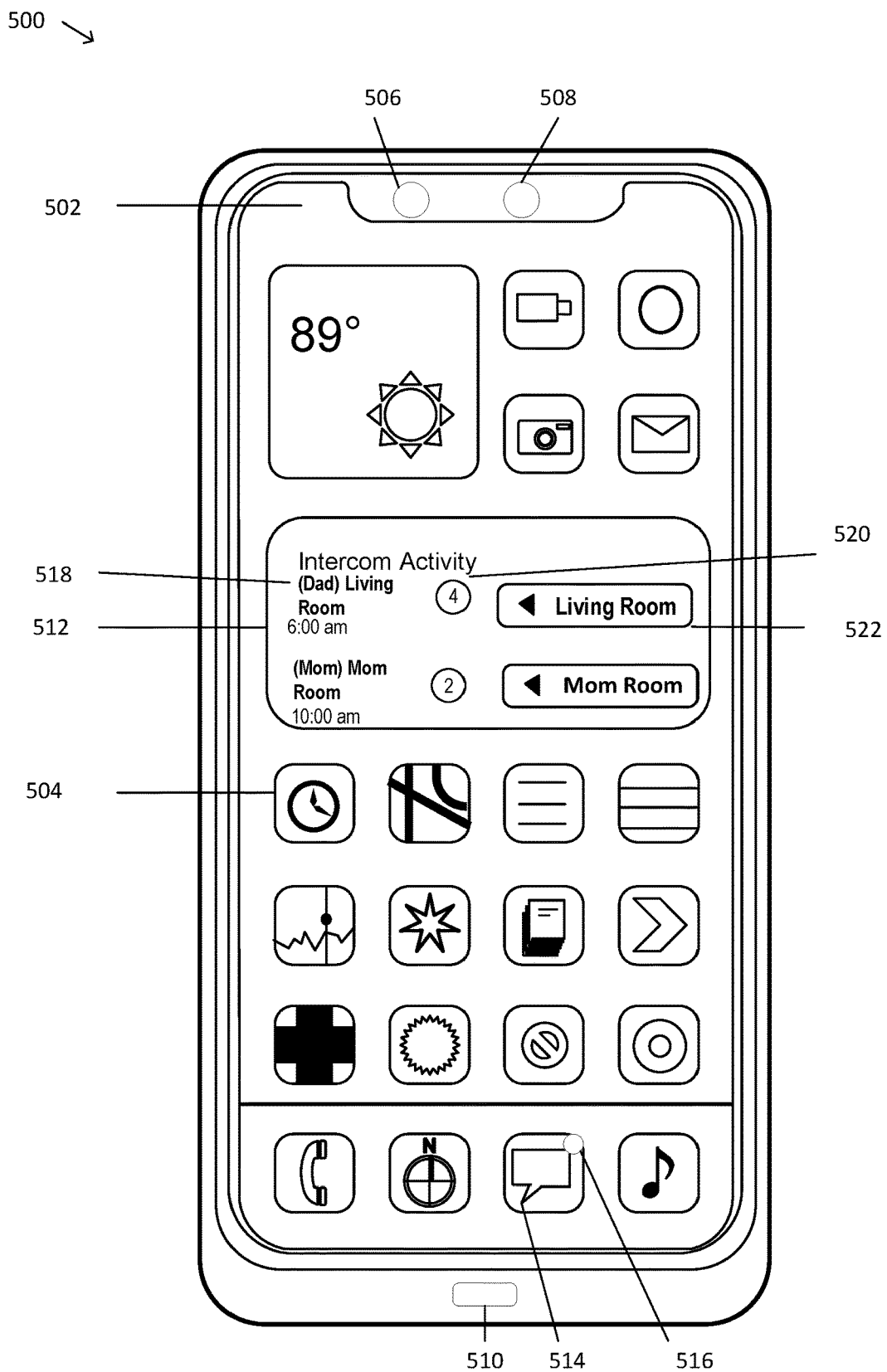
FIG. 5 is a diagram of a computing device for receiving an intercom message and a notification, according to one or more embodiments.

FIG. 5 is a diagram of a computing device for receiving an intercom message and a notification, according to one or more embodiments. The user device 500 can be, for example, any suitable computing device such as a smartwatch or smartphone. For example, the user device 500 can be the first user device 104 or the second user device 114 of FIG. 1. The user device 400 can also be the first user device 216 or the second user device 220 of FIG. 2. The user device 400 can include a display 402 for displaying a message (e.g., a health event message). The display 402 can include touch sensor technology for converting a touch to an electronic signal. The display 402 can be configured to display one or more application icons 404. In some embodiments, the user device 400 can include an image-capturing device 406, a microphone 408, and a speaker 410.

The user device 400 can be configured to display a widget 412 on the display 402. The widget 412 can be an extension of an application executing on the user device 400. The widget can further be larger than the one or more application icons 404. The message can be configured to display on the widget 412. For example, a resident device can include computer-readable instructions along with the message to display the event as a widget rather than as an SMS message, email message, or other message type. Since the person experiencing the event wants assistance from someone, the message can be displayed in a manner to prevent the message from being lost amongst other message types. As seen in FIG. 4, if an SMS application icon 414 included a visual push notification 416 that an SMS message had been received, the message would be hidden behind the SMS application 414. A user would still have to access the message through the SMS application, and possibly sift through multiple SMS messages before seeing the message.

The widget 412 can display one or more messages. The widget 412 can further provide a prompt to access a recording of a person wanting assistance. As illustrated, the widget 412 is displaying a message 418 for a person wanting assistance. The message 418 can include a location of the person wanting assistance in the home environment. The message 418 can further include an identity of the person wanting assistance. As illustrated, the person wanting assistance is dad and he is in the living room. The widget 412 can further present a queue icon 420 displaying a number of messages from the person wanting assistance. In some embodiments, the widget 412 displays the message 418 as a first message in a plurality of messages due to the urgent nature of the person wanting assistance. The widget 412 can further be configured to rearrange a presentation order of the number of messages based on the message being a higher priority. For example, a widget can hold one or more messages unrelated to the event prior to receiving the message 418. The messages unrelated to the event can be ordered based on various parameters, such as arrival time, sender, or message type. Upon receipt of the message 418, the widget 412 can be configured to override the ordering parameter(s) such the message 418 is displayed at the beginning of any order. In other words, the widget 412 can be configured to implement a priority ordering parameter, in which the message 418 is displayed as a first message in a queue of messages and displayed above any other messages. As an illustration, referring to FIG. 4, the widget 412 is displaying a message from dad above a message from mom. The message from mom can be a message unrelated to an event, and the message from dad can be an event message. Regardless of when the messages from mom and dad are received, and regardless of any other parameter, the widget 412 can be configured to position the messages from dad above mom based on the message from dad being an event message. Additionally, if the messages from mom and dad are ordered in a queue, the message from dad can be ordered as a first message, regardless of an ordering parameter that would order the message from mom higher than the message from dad.

The widget 412 can further present a recording icon 422 for presenting a recording of the person wanting assistance. A person can click on an icon and listen or watch a recording of the person wanting assistance. The recording icon 422 further includes a location in the home environment where the recording was made. The widget 412 can further provide an emergency medical services icon. A user can click on the emergency services icon, and the user device 400 can contact emergency medical services.

Figure 6:
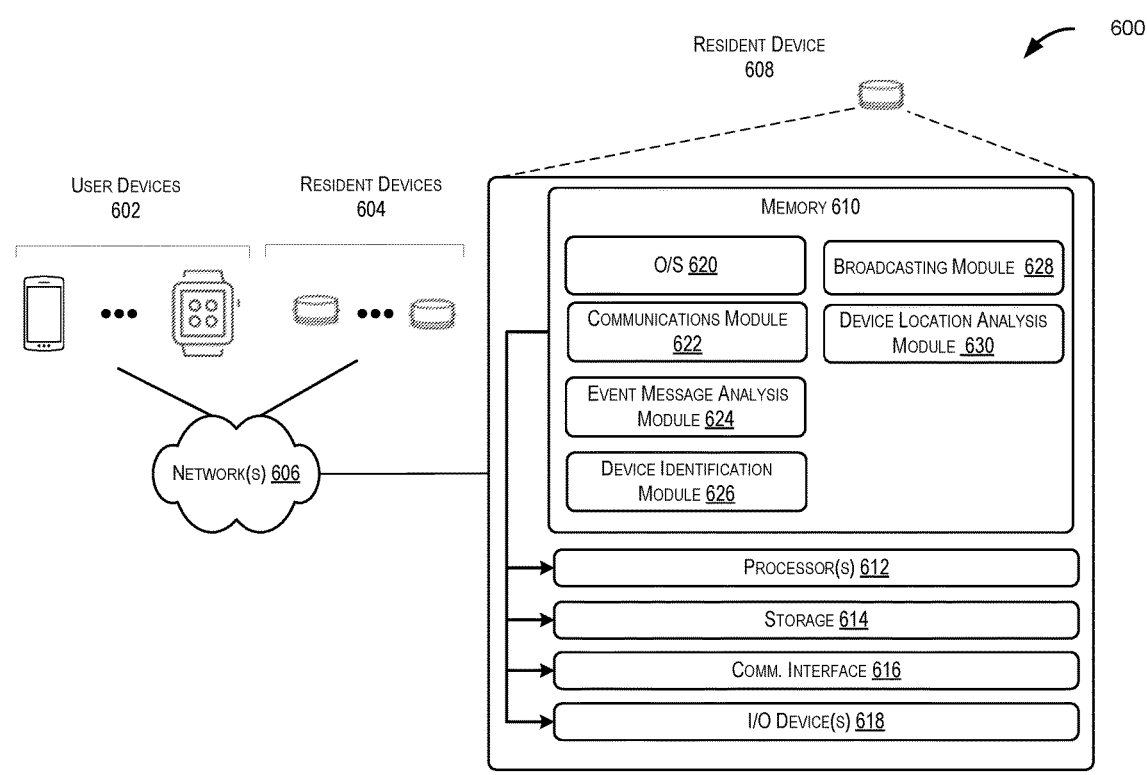
FIG. 6 is a diagram of a resident device, according to one or more embodiments.

FIG. 6, is a diagram of a resident device, according to one or more embodiments. The diagram 600 includes one or more user devices 602, one or more resident devices 604, one or more network(s) 606, and a representative resident device 608 (which may include one of the one or more resident devices 604). Each of these elements depicted in FIG. 6 may be similar to one or more elements depicted in other figures described herein. For example, the user devices 602 may be similar to any of the other user devices described herein and so forth. In some embodiments, at least some (e.g., and/or all) elements of diagram 600 may operate within the context of a home environment (e.g., home environment 202 of FIG. 2).

Turning to each element in further detail, a user device of the user devices 502 may be any suitable computing device (e.g., a mobile phone, tablet, personal computer (PC), smart glasses, a smartwatch, etc.). In some embodiments, a user device may perform any one or more of the operations of user devices described herein. Depending on the type of user device and/or location of the user device (e.g., within the home environment or outside the home environment), the user device may be enabled to communicate using one or more network protocols (e.g., a Bluetooth connection, a Thread connection, a ZigBee connection, an Infrared connection, a Wi-Fi connection, etc.) and/or network paths over the network(s) 606 (e.g., including a LAN and/or WAN), described further herein. In some embodiments, a user device will be connected to another device (e.g., a TV), through which the user device may provide data (e.g., notification messages, instructions, user interfaces) for presentation.

In some embodiments, the resident device 604 may correspond to any one or more of the resident devices described herein. For example, the resident device 604 may correspond to one or more of the resident devices of the home environment 202 of FIG. 2. Each resident device 504 may be any suitable computing device (e.g., a mobile phone, tablet, a smart speaker device, a smart media player communicatively connected to a TV, etc.). In some embodiments, a resident device may be positioned in a particular location (e.g., a room) of the home environment.

In some embodiments, the one or more network(s) 606 may include a WAN (e.g., the Internet) and/or a LAN. As described herein, the home environment may be associated with the LAN, whereby devices present within the home environment may communicate with each other over the LAN. As described herein, the WAN may be external from the home environment. For example, a router associated with the LAN (and thus, the home environment) may enable traffic from the LAN to be transmitted to the WAN, and vice versa. In some embodiments, the resident devices 604 may typically be resident within the home environment and communicate with other devices of the home environment over the LAN. In some embodiments, the user devices 602 may be transient. For example, as described herein, a user device may be present within the home environment (e.g., and communicate over the LAN), while, in another example, the user device may be outside the home environment and communicate over the Internet (or other suitable network).

As described herein, the resident device 668 may be representative of one or more resident devices of the resident devices 604. The resident device 608 has at least one memory 610, one or more processing units (or processor(s)) 612, a storage unit 614, a communications interface 616, and an input/output (I/O) device(s) 618.

Turning to each element of the resident device 608 in further detail, the processor(s) 512 may be implemented as appropriate in hardware, computer-executable instructions, firmware, or combinations thereof. Computer-executable instruction, or firmware implementations of the processor(s) 612 may include computer-executable or machine-executable instructions written in any suitable programming language to perform the various functions described.

The memory 610 may store program instructions that are loadable and executable on the processor(s) 612, as well as data generated during the execution of these programs. Depending on the configuration and type of the resident device 608, the memory 610 may be volatile (such as random access memory (RAM)) and/or non-volatile (such as read-only memory (ROM), flash memory, etc.). In some implementations, the memory 510 may include multiple different types of memory, such as static random access memory (SRAM), dynamic random access memory (DRAM), or ROM. The resident device 508 may also include additional storage 614, such as either removable storage or non-removable storage including, but not limited to, magnetic storage, optical disks, and/or tape storage. The disk drives and their associated computer-readable media may provide non-volatile storage of computer-readable instructions, data structures, program modules, and other data for the computing devices. In some embodiments, the storage 614 may be utilized to store data contents received from one or more other devices (e.g., other resident devices 604, and/or user devices 602). For example, the storage 614 may store user profiles of users affiliated with the home environment. The storage 614 may also store configuration settings, for example, indicating instructions for transmitting messages to devices affiliated with the home environment.

The resident device 608 may also contain the communications interface 616 that allows the resident device 608 to communicate with a stored database, another computing device or server, user terminals, and/or other devices on the network(s) 606. The resident device 608 may also include I/O device(s) 618, such as for enabling connection with a keyboard, a mouse, a pen, a voice input device, a touch input device, a display, speakers, a printer, etc. In some embodiments, the I/O devices(s) 618 may be used to output information related to an event message. This may include, but is not limited to, a recording of a person wanting assistance, or mitigation steps.

Turning to the contents of the memory 610 in more detail, the memory 610 may include an operating system 620 and one or more application programs or services for implementing the features disclosed herein, including a communications module 622, a message analysis module 624, a device identification module 626, a broadcasting module 628, and a device location analysis module 630. In some embodiments, any one or more of the application programs or services of resident device 608 (or any other features of resident devices described herein) may be used to implement the event messaging service.

The communications module 622 may comprise code that causes the processor 612 to generate messages, forward messages, reformat messages, and/or otherwise communicate with other entities. For example, as described herein, the communications module 622 may transmit and/or receive messages to/from other user devices 602 and other resident devices 604. As described herein, the communications module 622 may transmit messages via one or more transmission protocols.

The message analysis module 624 may comprise code that causes the processor 612 to receive and process a message. In some embodiments, one or more of the operations of message analysis module 624 may be similar to those described herein. For example, the message analysis module 624 may also determine, for example, an identity of a person wanting help, the person's location, and other suitable information from the message.

The device identification module 626 may comprise code that causes the processor 612 to identify one or more devices in the home environment. For example, the device identification module 626 may retrieve one or more user profiles (e.g., from storage 614) and identify one or more devices associated with each user profile. In another example, the device identification module 626 may further identify one or more candidate recipient devices based on device location and/or proximity data, as described below regarding the device location analysis module 630.

The broadcasting module 628 may comprise code that causes the processor 636 to transmit the message throughout the home environment. In some embodiments, the presentation of the message may be similar to as described in reference to FIGS. 1 and 2. In some embodiments, the transmission of the message may depend in part on the type of recipient device (e.g., a mobile phone, a smartwatch, a smart speaker, etc.). In some embodiments, a notification and/or announcement may be presented (or suppressed) based in part on a setting that is stored on the resident device 608 (and/or a setting of the recipient device).

The device location analysis module 630 may comprise code that causes the processor 612 to determine a location of a particular device. In some embodiments, one or more of the operations of device location analysis module 630 may be similar to those described in reference to FIGS. 1 and 2. For example, the device location analysis module 630 may receive location information from one or more user devices 602 and/or resident devices 604, which is used to determine the location of each device.

Figure 7:
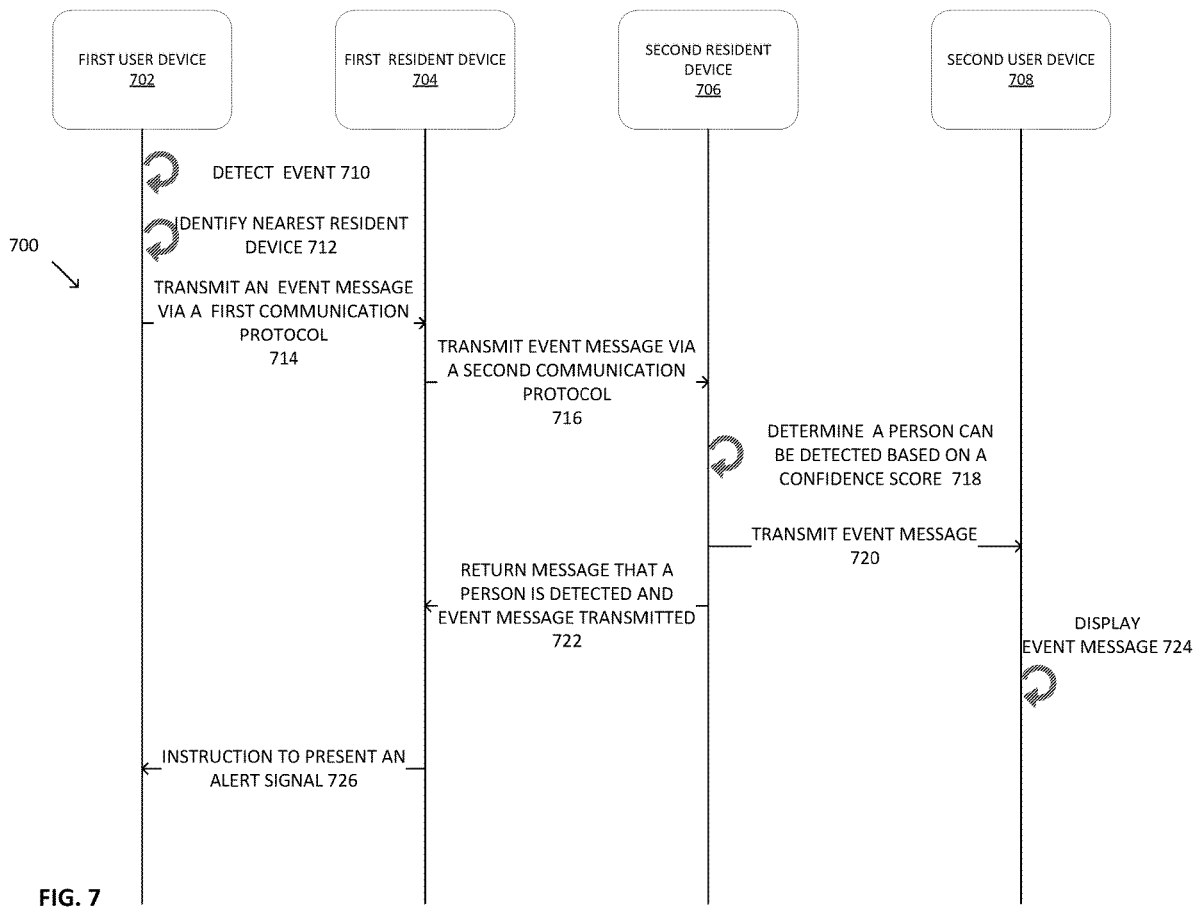
FIG. 7 is a signaling diagram for an in-home intercom and notification system, according to one or more embodiments.

FIG. 7 is a signaling diagram 700 for an in-home intercom and notification system, according to one or more embodiments. As shown in FIG. 7, a first user device 702, a first resident device 704, a second resident device 706, and a second user device 708 can interact with each other. While the operations of processes 700, 800, 900, 1000, 1100, 1200, 1300, and 1400 are described as being performed by computing devices, it should be understood that any suitable device (e.g., a user device, a resident device) may be used to perform one or more operations of these processes. Processes 700, 800, 900, 1000, 1100, 1200, 1300, and 1400 (described below) are respectively illustrated as logical flow diagrams, each operation of which represents a sequence of operations that can be implemented in hardware, computer instructions, or a combination thereof. In the context of computer instructions, the operations represent computer-executable instructions stored on one or more computer-readable storage media that, when executed by one or more processors, perform the recited operations. Generally, computer-executable instructions include routines, programs, objects, components, data structures, and the like that perform particular functions or implement particular data types. The order in which the operations are described is not intended to be construed as a limitation, and any number of the described operations can be combined in any order and/or in parallel to implement the processes.

At 710, a first user device 702 can detect an event. The event can be a health-related experience of a person in a home environment. For example, a person in a kitchen may experience stroke-like symptoms. The first user device 702 can be a computing device located in a home environment. In response to detecting an event, the first user device 702 can generate an event message (e.g., a health event message). The message can include an identity of the user account associated with the first user device 702, a description of the event, and a location of the first user device 702.

At 712, the first user device 702 can detect the nearest resident device. In some embodiments, the first user device 702 is connected to a network, such as a Wi-Fi network and stores the address and identifier for each other network device that it discovers. The first user device 702 can search its memory for the last discovered resident device. In other embodiments, the first user device can transmit a signal requesting a return signal from any other device. The first user device 702 can determine the nearest resident device based on a strength of a response signal.

At 714, the first user device 702 can transmit the message to a first resident device 704. The first resident device 704 can be the nearest device to the first user device 702. The first user device 702 can transmit the message via a first transmission protocol. The first transmission protocol can be a short-range transmission protocol. The first user device 702 can preserve battery life by transmitting the message over the first transmission protocol.

At 716, the first resident device 704 can transmit the message to a second resident device 706. In addition, the first resident device 704 can include computer-readable instructions for the second resident device 706 to determine whether it can detect a person. It should be appreciated that the first resident device 704 can transmit the message and instructions to each other resident device in the home environment.

At 718, in some embodiments, the second resident device 706 can determine whether it can detect a user device and further detect a person. The second resident device 706 can make these determinations based on various factors. For example, the second resident device 706 can scan its memory to determine the last time that it discovered another device in the home environment. If the time elapsed since the discovery is below a threshold time and the device is associated with a person, the second resident device 706 can determine a user device is present. The second resident device 706 can determine the last time it received a signal from the user device. If the time elapsed since the discovery is less than a threshold time and the device is associated with a person, the second resident device 706 can determine a person is present, based on a confidence score. If the time elapsed since the discovery is greater than a threshold time and the device is associated with a person, the second resident device 706 can determine a person is not present based on a confidence score.

At 720, the second resident device 706 can transmit the message to the second user device 708. At 722, the second resident device 706 can transmit a message that it detected a person and transmitted the message. At 724, the second user device 708 can present the message. For example, the second user device 708 can include a display and can display the message.

At 726, the first resident device 704 can transmit a message to the first user device 702 to present an alert signal. In some embodiments, the first user device 702 can project an audio or visual alert signal in response to this message.

Figure 8:
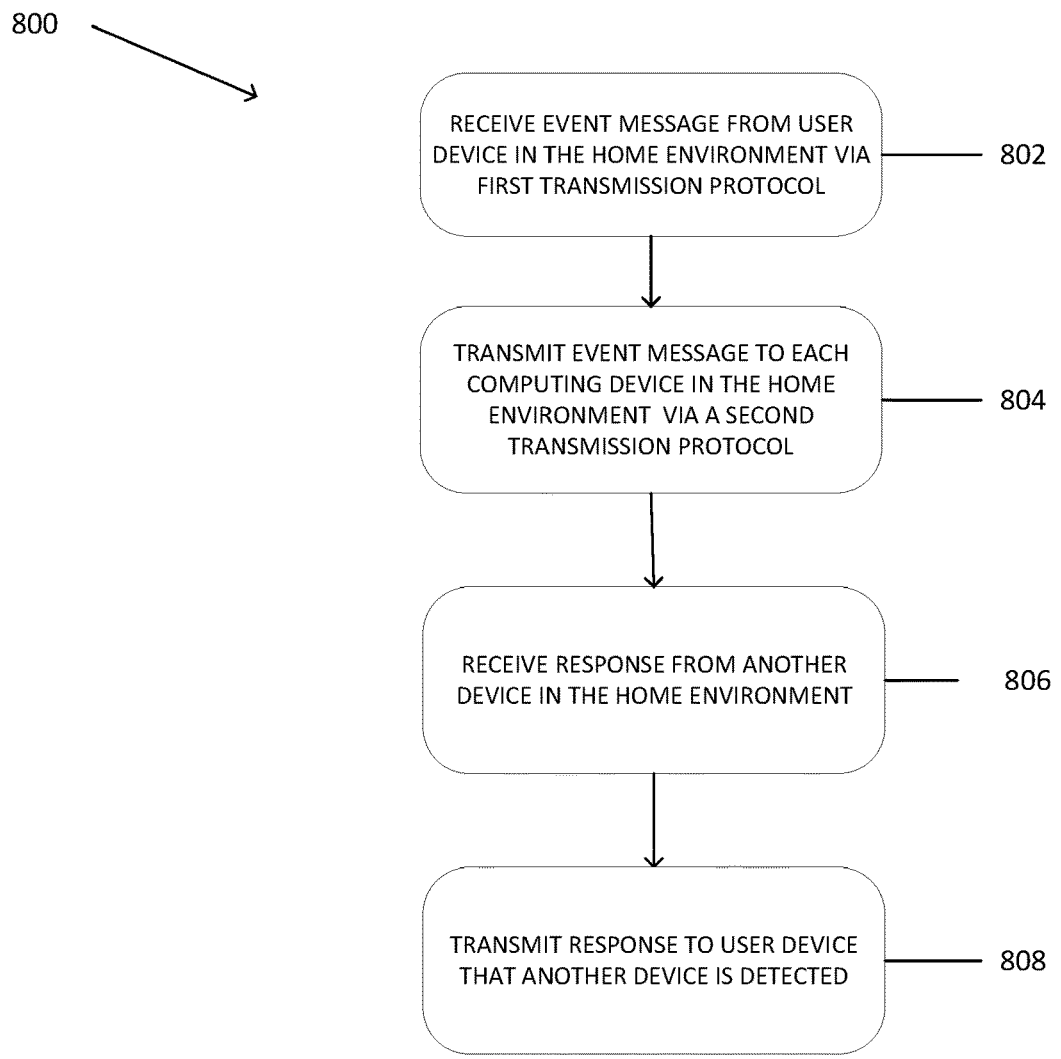
FIG. 8 is a process flow an in-home intercom and notification system, according to one or more embodiments.

FIG. 8 is a process flow 800 an in-home intercom and notification system, according to one or more embodiments. At 802, a computing device can receive an event message (e.g., a health event message) from a user device. The computing device can be, for example, a resident device that communicates with other devices in a home environment (e.g., first resident device 106 of FIG. 1 or first resident device 210 of FIG. 2). The message can describe an event experienced by someone in the home environment. The message can include an identity of the person experiencing the event, and a location of a user device.

At 804, the computing device can transmit the message to other computing devices in the home environment via a second transmission protocol. The other computing devices can also be resident devices (e.g., second resident device 110 and third resident device 112 of FIG. 1, and second resident device 212 and third resident device 214 of FIG. 2) located in various locations in the home environment. In some embodiments, the computing device further transmits instructions for each other computing device to determine whether they can detect a person.

At 806, the computing device can receive a response from at least one of the other computing devices. The response can include a notification that the event message has been transmitted to a user device.

At 808, the computing device can transmit a message to the user device associated with the person experiencing the event that the at least one computing device detected a person. In some embodiments, the message can include instructions for the user device to present an alert signal to assist people in finding the person experiencing the event.

Figure 9:
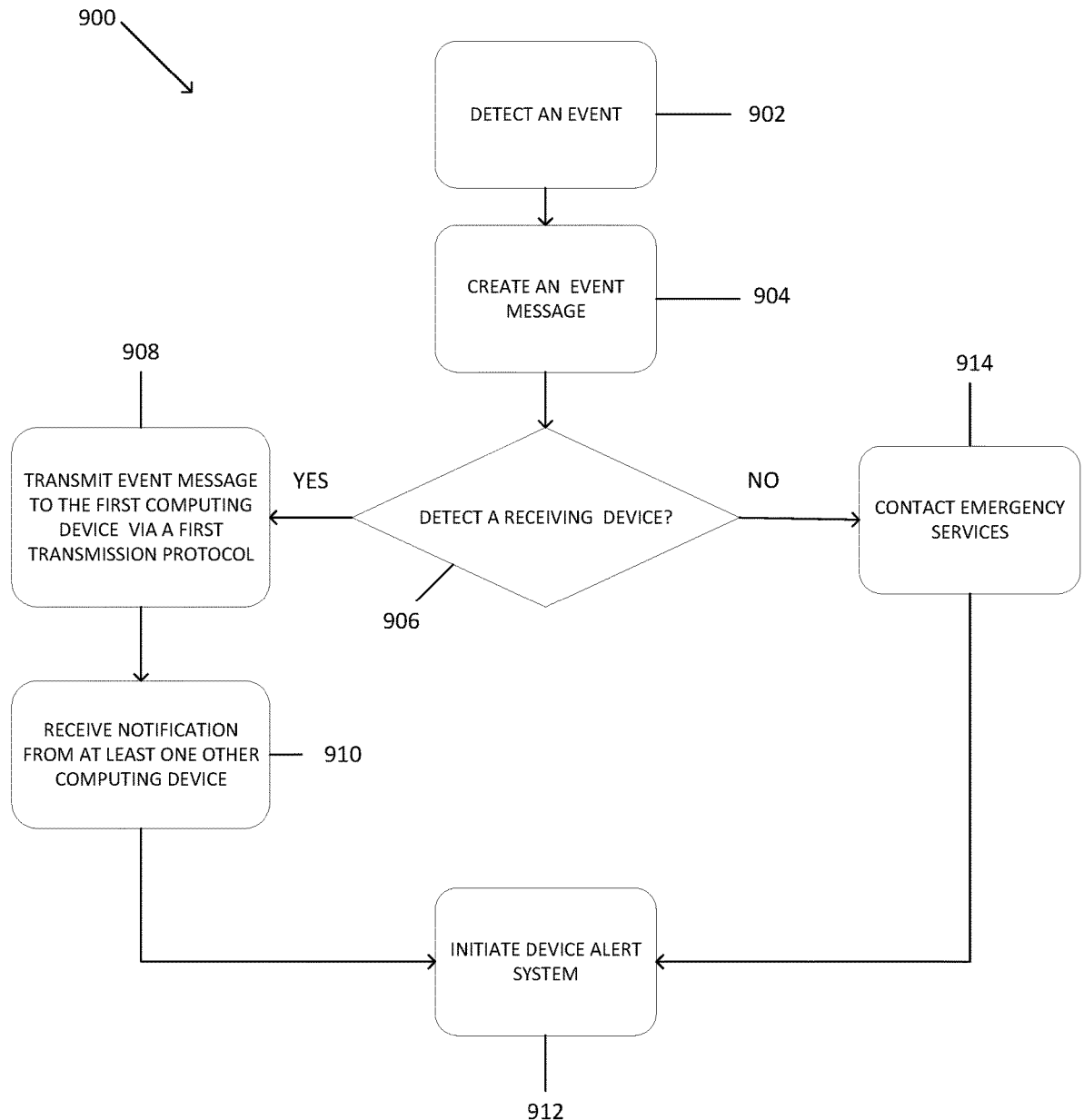
FIG. 9 is a process flow for an in-home intercom and notification system, according to one or more embodiments.

FIG. 9 is a process flow 900 for an in-home intercom and notification system, according to one or more embodiments. At 902, a computing device can detect that a person is experiencing an event. The computing device can be a first user device located in a home environment (e.g., first user device 104 of FIG. 1 or first user device 216 of FIG. 2). The computing device can be equipped with sensors such as biometric sensors, audio sensors, image-capturing sensors. Based on data collected by the sensors, the computing device can determine that a person is experiencing an event. The person can be a user that has a user account associated with the computing device. The computing device can further determine the nature of the event. For example, if the person is sleeping and their breathing slows down, the computing device can determine that the person may be experiencing sleep apnea.

At 904, in response to detecting the event, the computing device can create an event message (e.g., a health event message). The message can include an identity of the person associated with the user account, a description of the event, and a location of the computing device in the home environment.

At 906, the computing device can determine whether it can detect a receiving device within a short range. The search for the device within a short range can be based on determining that the event occurred. In other words, the indication that a person may be injured can trigger the search for a device can notify another person within a shoer distance to render assistance. The short range can be a range whereupon the computing device can communicate with the receiving device via a short-range transmission protocol. The receiving device can be any device that is connected to a network of the home environment. For example, the receiving computing device can be a resident device in the home environment (e.g., first resident device 116 of FIG. 1 or first resident device 210 of FIG. 2). The computing device can use various techniques to determine whether it can detect the receiving device. For example, the computing device can send out a signal via a first transmission protocol, such as a short-range transmission protocol (e.g., Bluetooth). The computing device can determine a distance between the computing device and the receiving device based on a strength of a signal response. The computing device can also include an identity of each computing device that it has discovered in the home environment. For example, if the computing device is a smartwatch worn by a person, the smartwatch can store an identity of each other computing device it discovers as the person walks around the home environment. The computing device can determine that the last detected device is the closest device.

If the computing device detects a receiving device, the process 900 proceeds to step 908. At 908, the computing device can transmit the message to the receiving device via the first transmission protocol. The first transmission protocol can be a short-range transmission protocol, such as Bluetooth. The computing device can conserve power by transmitting the message via the first transmission protocol rather than a second transmission protocol, such as Wi-Fi or cellular.

At 910, the computing device can receive a notification that a user device associated with a second person has been detected. The notification can be received from the receiving device. The notification can further include instructions to present an alert signal, such as an audio, visual, or vibratory signal. At 912, the computing device can initiate a device alert system and present the alert signal.

If at 906, the computing device did not detect a receiving device, the computing device can contact emergency medical services at 914. The computing device can also initiate an alert system and present the alert signal at 912.

Figure 10:
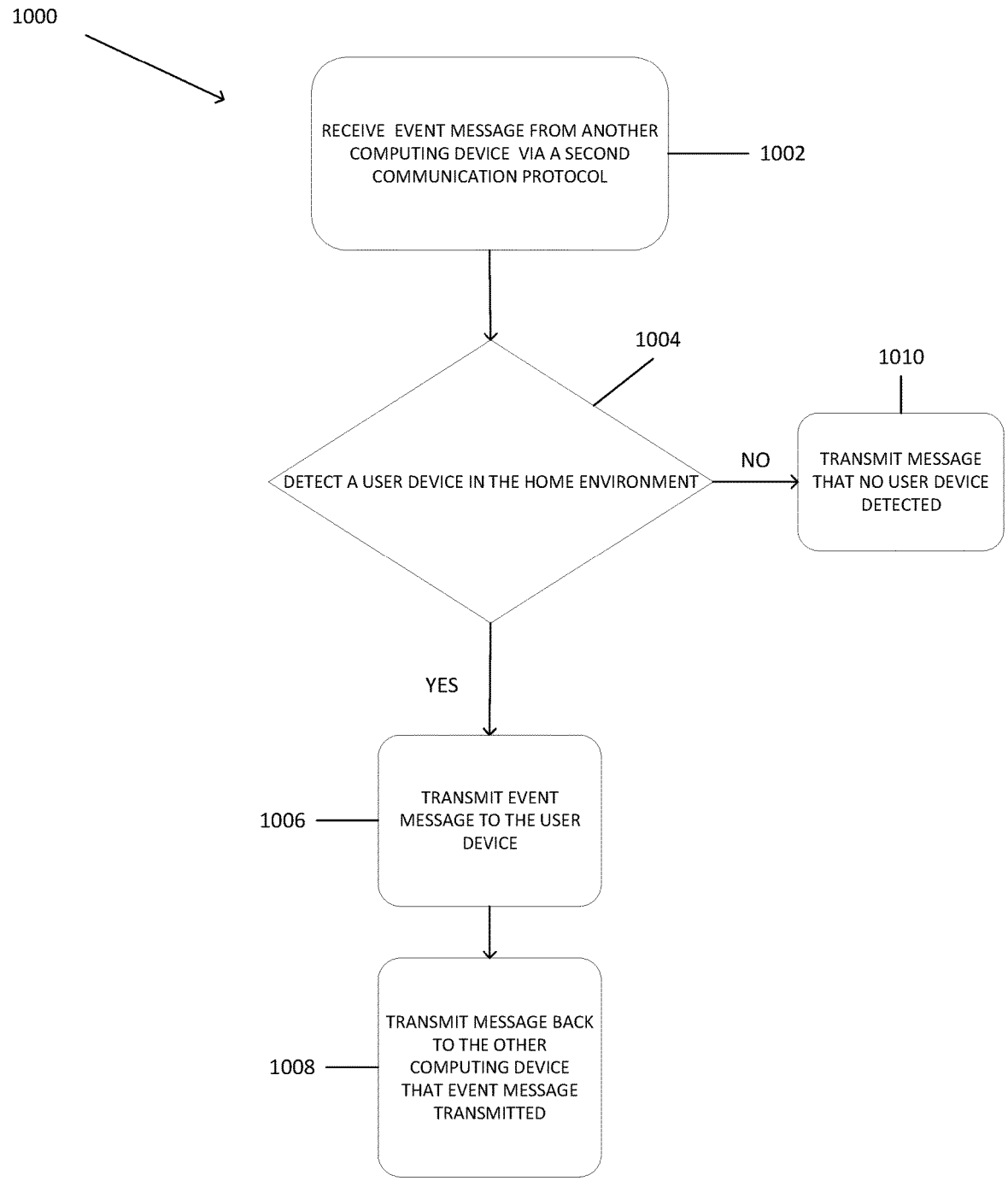
FIG. 10 is a process flow for transmitted an event message by an in-home intercom and notification system, according to one or more embodiments.

FIG. 10 is a process flow 1000 for an in-home intercom and notification system, according to one or more embodiments. At 1002, a computing device can receive an event message (e.g., a health event message). The computing device can be a resident device in a home environment (e.g., second resident device 110 of FIG. 1 or second resident device 212 of FIG. 2). The message can be received from another resident device (e.g., first resident device 116 of FIG. 1 or first resident device 210 of FIG. 2). The message can include instructions to determine whether a person can be detected.

At 1004, the computing device can determine whether a person can be detected. The determination can be based on whether the computing device detects a user device, and whether the data suggests that a person is more likely than not to be present. The computing device can initiate the search for the user device based on determining that the message received is an event message. Therefore, it is likely that a person may need assistance. For example, the computing device can detect an identifier indicating that the message is an event message. Based on the detection, the computing service can perform the search for the user device. The computing device can use various techniques to detect whether a user device is present. In instances that the computing device is connected to a network, the computing device can discover other devices. In each instance that the computing discovers another computing device, the computing device can store the discovery in its local memory. Therefore, the computing device can scan its local memory and determine if it has discovered another device.

If, at 1004, the computing device detects another user device, the process 1000 proceeds to 1006. At 1006, the computing device transmits the event message to the other user device. The event message can be sent using a different transmission protocol that the transmission protocol used to receive the event message for the device of the person needing assistance. For example, if the transmission protocol used to receive the message can be Bluetooth. Bluetooth can be advantageous because it can consume less power than, for example, Wi-Fi. The person needing assistance's device is likely battery powered and can need to conserve as much power as possible to continue to be able to transmit event messages. On the other hand, the computing device is likely drawing power from an electrical socket, and therefore afford to use a more power consuming transmission protocol. The more power consuming protocol may permit the computing device to detect a user device at a greater distance than the transmission protocol (e.g., Bluetooth) used to receive the message. The computing device can switch to the more power consuming transmission protocol (e.g., Wi-Fi) based on determining that the message is an event message. For example, the computing device can detect an identifier that is indicative that the message is an event message. Based on the detection, the computing device can select the more power consuming transmission protocol (e.g., Wi-Fi).

At 1008, the computing device can transmit a message to back the other resident device that a user device has been detected and that the message has been transmitted. The message can be transmitted using the transmission protocol used to receive the message (e.g., Bluetooth).

If, at 1004, the computing device does not detect a user device, the computing device can transmit a message back to the other computing device that no person was detected at 1010. This could occur in a situation in which a computing device has recently been introduced into a network and no traffic has passed by the device.

Figure 11:
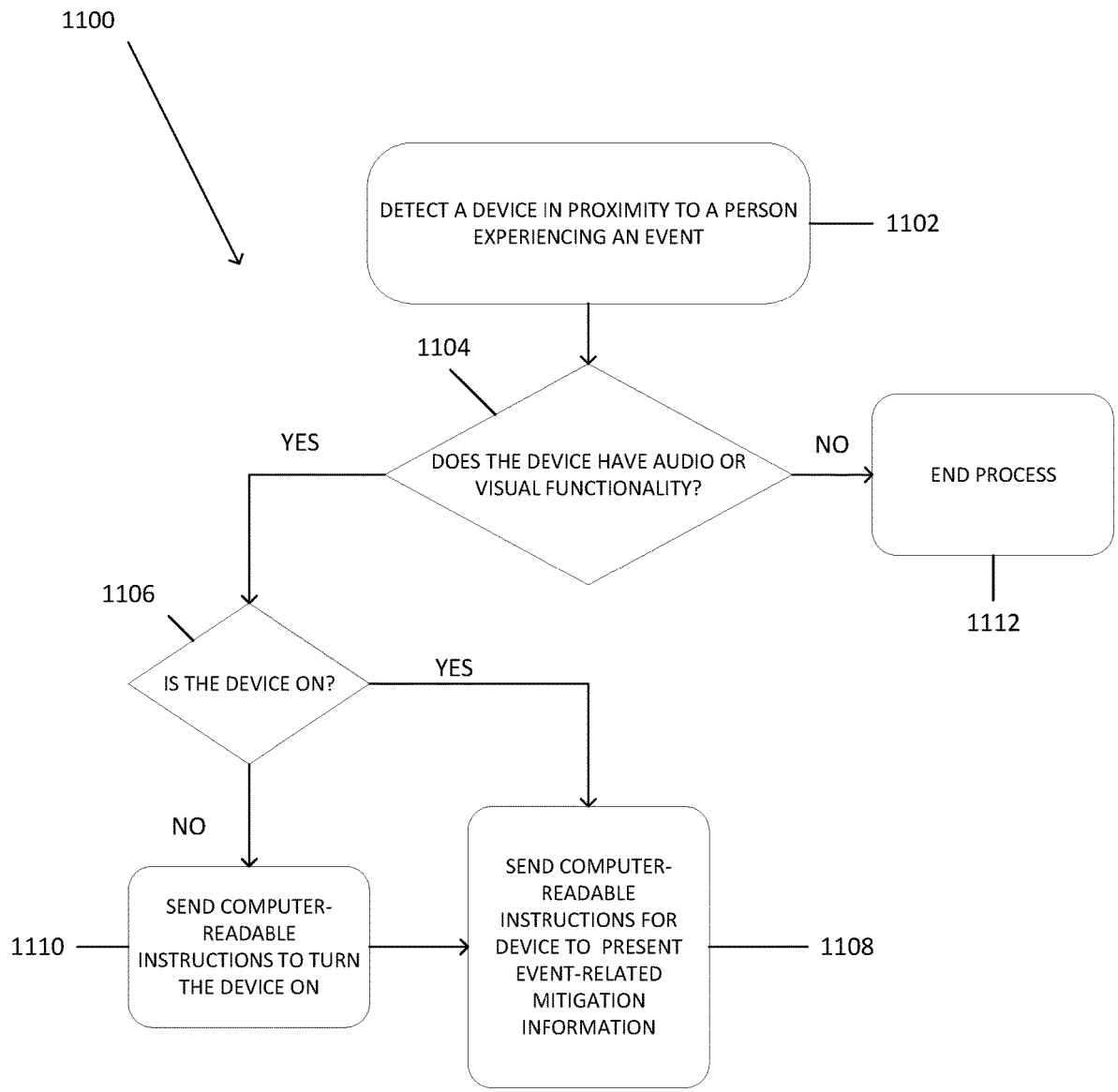
FIG. 11 is a process flow for providing event-related mitigation by an in-home intercom and notification system, according to one or more embodiments.

FIG. 11 is a process flow 1100 for an in-home intercom and notification system, according to one or more embodiments. At 1102, the computing device can detect a device in proximity to a person experiencing an event. For example, the computing device can transmit a signal via a first transmission protocol and then determine a distance based on a strength of a signal response. If the determined distance is less than a threshold distance, the computing device can determine that the device is proximate to the person experiencing an event. The computing device can be, for example, a first resident device (e.g., first resident device 116 of FIG. 1 or first resident device 210 of FIG. 2). The device can be, for example, another resident device (e.g., fourth resident device 224 of FIG. 2).

At 1104, the computing device can communicate with the device and determine whether it has audio or visual capability. If at 1104, the computing device determines that the device does have audio or visual capability, the process 1100 proceeds to 1106. At 1106, the computing device can determine whether the device is on. In particular, whether the device is in a sleep mode or a presentation mode.

If the computing device determines that the device is in a presentation mode, the process 1100 proceeds to 1108. At 1108, the computing device can transmit computer-readable instructions to the device to present event-related mitigation information. For example, if the person has fallen, the device can present a video or audio recording that describes how to help someone back to their feet without injuring them. If, however, the computing device determines that the device is in a sleep mode, the computing device can send computer-readable instructions to turn the device to a presentation mode at 1110. The computing device can then transmit computer-readable instructions to the device to present event-related mitigation information. If, however, at 1104, the computing device determined that the device does not have audio or visual capability, the process 1000 ends at 1112.

Figure 12:
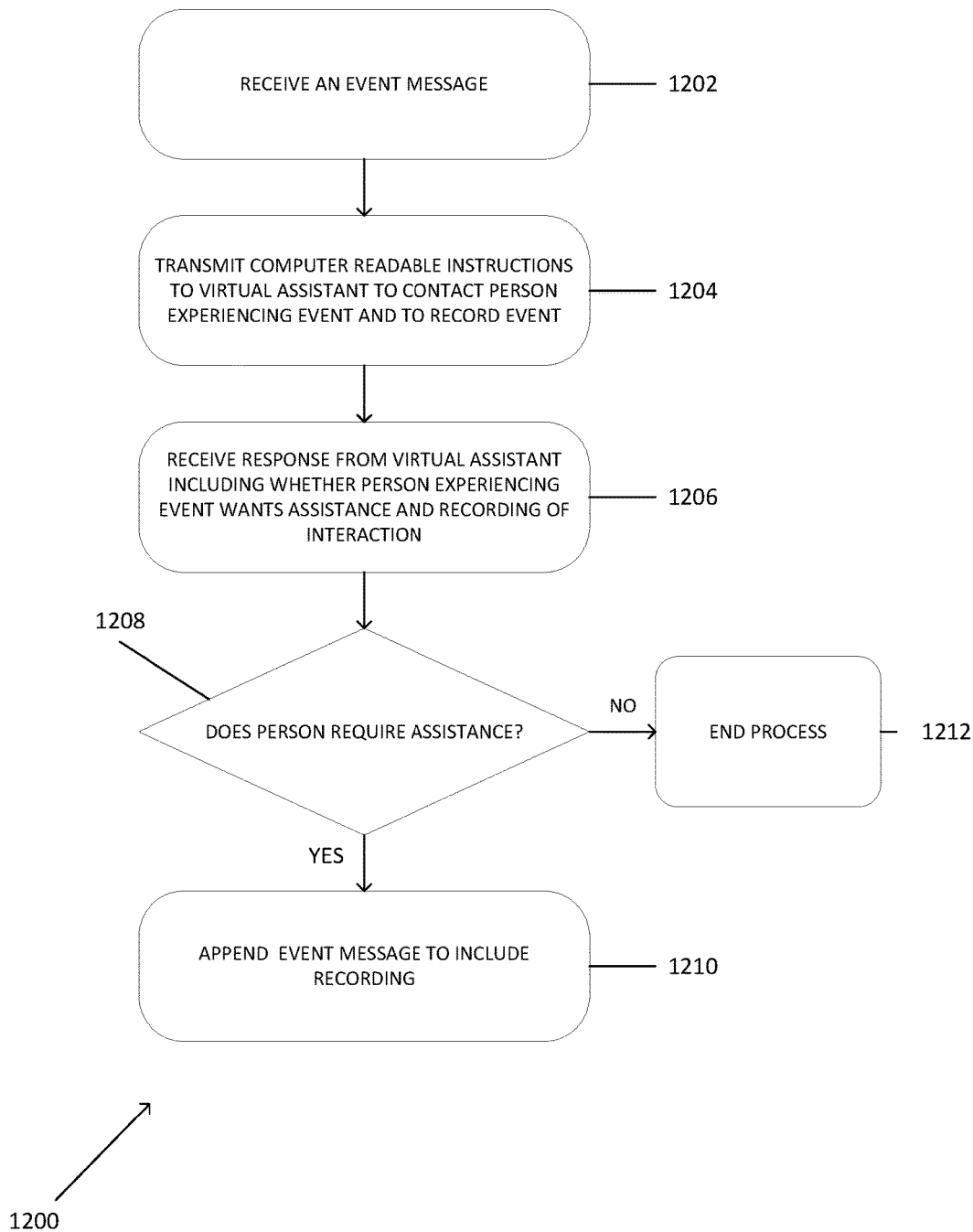
FIG. 12 is a process flow for an in-home intercom and notification system, according to one or more embodiments.

FIG. 12 is a process flow 1200 for an in-home intercom and notification system, according to one or more embodiments. At 1202 a computing device can receive an event message (e.g., a health event message). The event message can include an identifier that indicates that the message is an event message. The computing device can be, for example, a first resident device, (e.g., first resident device 116 of FIG. 1 or first resident device 210 of FIG. 2). In some embodiments, the computing device is integrated with a virtual assistant. Therefore, at 1204, the computing device can transmit computer-readable instructions to the virtual assistant to contact the person experiencing an event and ask them if they want assistance. For example, as seen in FIG. 1, the virtual assistant asks the first person 102, "Do you want help?"

At 1206, the computing device can receive a response from the virtual assistant as to whether the person wants assistance. In addition to the response, the computing device can receive a recording of the person wanting assistance. The recording can be, for example, an audio recording or a visual recording.

At 1208, the computing device can determine whether the person wants assistance. In some embodiments, the virtual assistant has access to software that translates the person's response into a determination of whether that person wants assistance. If, at 1208, the computing device determines that the person wants assistance based on the virtual assistant's analysis, the process 1200 proceeds to 1210.

At 1210 the computing device can append the message to include the recording. If, however, the computing device determines that the person does not want assistance based on the virtual assistant's analysis, the process 1200 ends at 1212.

Figure 13:
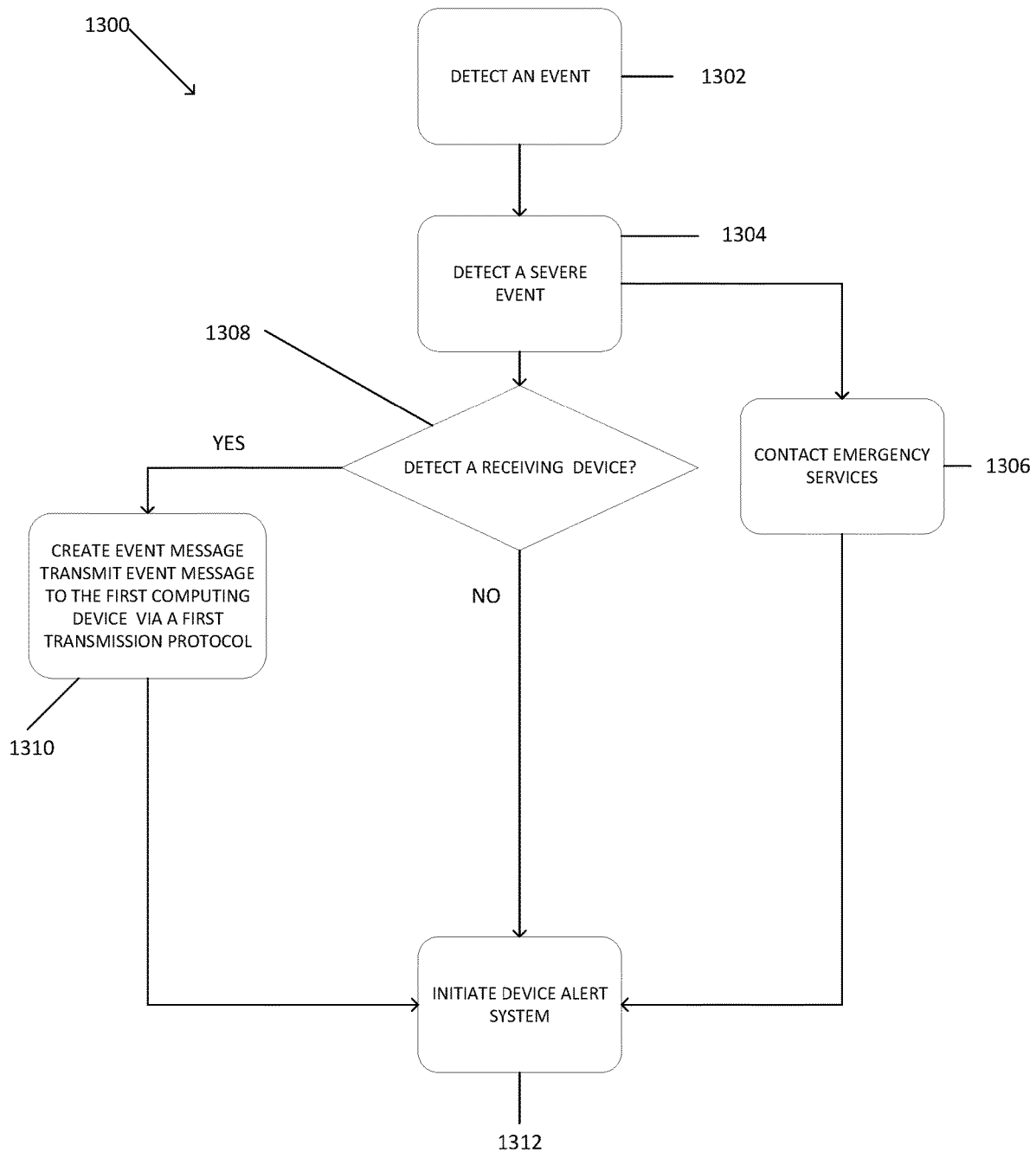
FIG. 13 is a process flow for detecting a severe event by an in-home intercom and notification system, according to one or more embodiments.

FIG. 13 is a process flow 1300 for an in-home intercom and notification system, according to one or more embodiments. At 1302, a computing device can detect that a person is experiencing an event. The computing device can be a first user device located in a home environment (e.g., first user device 104 of FIG. 1 or first user device 216 of FIG. 2). The computing device can be equipped with sensors such as biometric sensors, audio sensors, image-capturing sensors. Based on data collected by the sensors, the computing device can determine that a person is experiencing an event.

At 1304, the computing device can further detect the severity of the event. For example, the computing device can receive signal data from one or more sensors. The computing device can further access a mapping between a sensor-based signal and a table of severity. The computing device can perform a look up of the table and determine the severity of the event. If the event is not a severe event, the computing device can proceed as described with respect to FIG. 8. For example, the process 1300 can proceed to step 804 of FIG. 8. For purposes of illustration of the figure, it is presumed that the device detects the severe event. At this point, the computing device contacts emergency services (e.g., law enforcement, health care professions, hospital) at 1306. The computing device can contact emergency service, for example, via an internet-based service. Either after contacting emergency services or in parallel with contacting emergency services, the computing device determines whether it can detect a receiving device at 1308.

If the computing device cannot detect a receiving device, at 1312, the computing device can initiate a notification of a device alert system of the computing device. The notification can further include instructions to present an alert signal, such as an audio, visual, or vibratory signal.

If, however, the computing device does detect a receiving device (e.g., a user device), the process 1300 proceeds to 1310. At 1310, the computing device can create an event message (e.g., a health event message). The message can include an identity of the person associated with the user account, a description of the event, and a location of the computing device in the home environment. The computing device can transmit the message to the receiving device via the first transmission protocol.

The receiving device may or may not detect another person in the home environment. However, given the severity of the event, the computing device proceeds to 1312 regardless of whether the receiving device detects another person. At 1312, 1312 the computing device can initiate a notification of a device alert system of the computing device.

Figure 14:
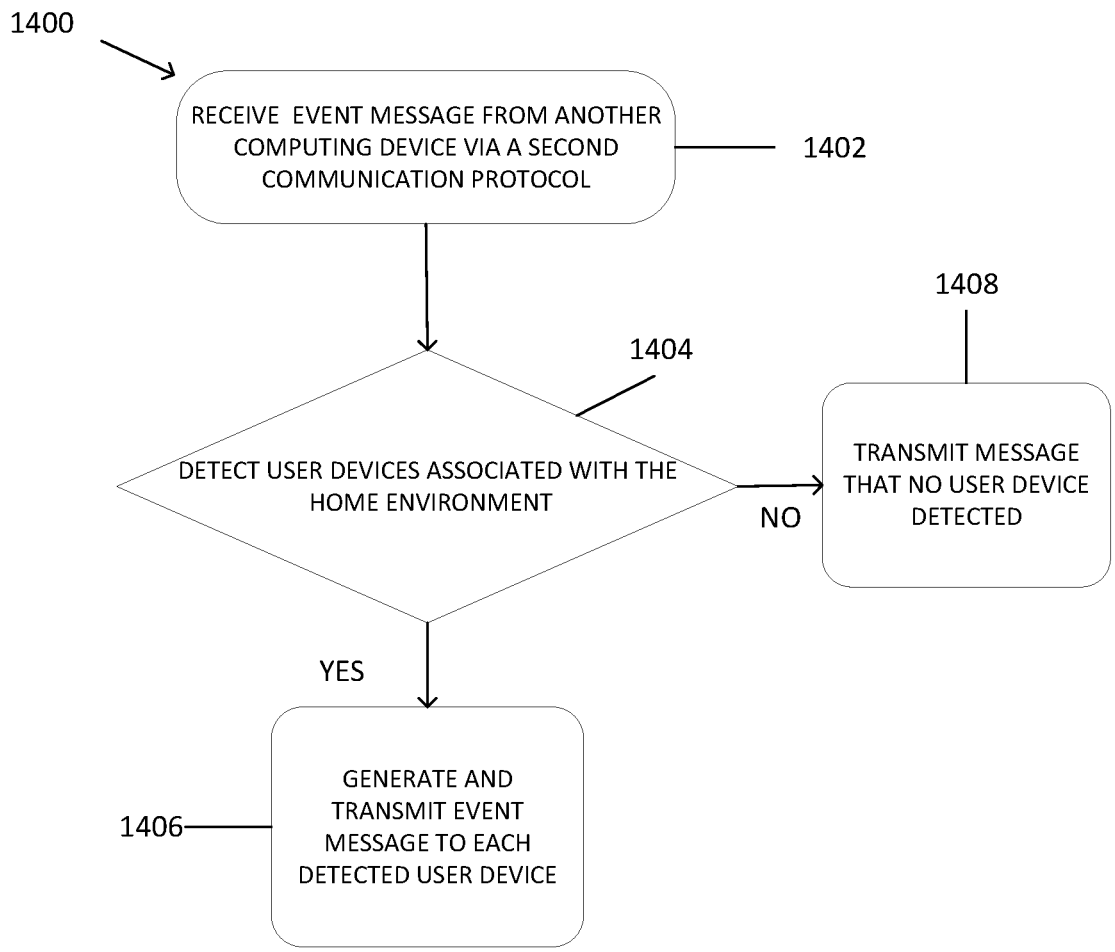
FIG. 14 is a process flow for detecting devices by an in-home intercom and notification system, according to one or more embodiments.

FIG. 14 is a process flow for detecting devices by an in-home intercom and notification system, according to one or more embodiments. At 1402, a computing device can receive an event message (e.g., a health event message). The computing device can be a resident device in an environment (e.g., home or office). The event message can include a recording of a first person requesting assistance or a recording of the computing device's surrounding in instances that the person cannot communicate. The message can further include a location of the source of the message. In addition to the recording and location, the message can further include an identity of the first person, a location of the first person in the home environment. The event message can further include instructions to determine whether any other person (e.g., second person, third person, fourth person) can be detected.

At 1404, the computing device can determine whether any other person can be detected. The determination can be based on whether the computing device detects a user device, and whether the data suggests that a person is more likely than not to be present based on the detection of the user device.

The computing device can use various techniques to detect whether other user devices are present in the environment (e.g., home or office). In instances that the computing device is connected to a network, the computing device can discover other devices connected to the network. In each instance that the computing discovers another computing device, the computing device can store the discovery in its local memory. Therefore, the computing device can scan its local memory and identify each discovered device. The computing device can further determine whether it is likely that a person is present based on the detection of the user device. For example, the computing device.

In addition to detecting user devices connected to the network, the computing device can detect user devices based on an association with a smart home platform (e.g., Apple HomeKit). The smart home platform can operate as an application on the computing device. The smart home platform can include multiple accounts and the computing device can use the smart home platform to identity user devices associated with each account.

If, at 1404, the computing device detects other user devices, the process can proceed to 1406. At 1406, the computing device can transmit the event message to each identified device. The computing device can also send an identification of each other identified device with the event message. It should be appreciated that if the computing device only detects one other user device, the computing device does not include the identity of the user device.

The computing device can transmit the event message and the other device identifications, to each identified user device. Therefore, each device receives the event message and the identity of each other device that received the event message.

The computing device can send the event message using a different transmission protocol that the transmission protocol used to receive the event message for the device of the person needing assistance. The computing device can use a variety of the more power consuming transmission protocols (e.g., cellular, Wi-Fi, Bluetooth, internet) based on determining that the message is an event message. The computing device can use different transmission protocols for different devices. For example, for devices in the same environment as the computing device can use a local network to transmit the event messages. In the event that a user device is outside the environment, the computing device can use a long range transmission protocol, such as cellular or internet.

If, at 1404, the computing device does not detect a user device, the process can proceed to step 1408. At 1408, the computing device can transmit a message back to the other computing device (e.g., the user device of the person that is in need of assistance) that no person was detected at 1404.

In some embodiments, the computing device can further provide healthcare-related information either directly or cause another device to provide the information. For example, the computing device can be in communication with another device such as a smart tv, media streaming device, or other smart speaker. The computing device can either directly or indirectly provide healthcare-related information related to the person. The information can be configured to provide assistance to someone provide assistance. For example, the information can be user-specific, such as medications that the person is allergic to. The information can situation-specific, such as CPR techniques in the instance that the event is, for example, choking.

While specific embodiments have been described, one skilled in the art will recognize that numerous modifications are possible. A single controller may use processes described herein to establish pairings with any number of accessories and to selectively communicate with different accessories at different times. Similarly, a single accessory may be controlled by multiple controllers with which it has established pairings. Any function of an accessory may be controlled by modeling the function as a service having one or more characteristics and allowing a controller to interact with (e.g., read, modify, receive updates) the service and/or its characteristics. Accordingly, protocols and communication processes as described herein may be "universal," meaning that they may be applied in any context with one or more controllers and one or more accessories regardless of accessory function or controller form factor, or specific interfaces.

Thus, although specific embodiments have been described, it will be appreciated that embodiments may include all modifications and equivalents within the scope of the following claims.

As described above, one aspect of the present technology is the gathering and use of data available from specific and legitimate sources to improve the delivery of messages from one device to one or more devices (e.g., delivering messages for an in-home health intercom). The present disclosure contemplates that in some instances, this gathered data may include personal information data that uniquely identifies or may be used to identify a specific person. Such personal information data may include demographic data, location-based data, online identifiers, telephone numbers, email addresses, home addresses, data or records relating to a user's health (e.g., vital signs measurements, medication information), date of birth, or any other personal information.

The present disclosure recognizes that the use of such personal information data, in the present technology, may be used to the benefit of users. For example, the personal information data may be used to deliver a command from a user profile on a computing device to one or more computing devices. Further, other uses for personal information data that benefit the user are also contemplated by the present disclosure. For instance, specific states of devices (e.g., healthcare-related devices, wearable devices, etc.) associated with the user may be transmitted from a device back to the user profile.

The present disclosure contemplates that those entities responsible for the collection, analysis, disclosure, transfer, storage, or other use of such personal information data will comply with well-established privacy policies and/or privacy practices. In particular, such entities would be expected to implement and consistently apply privacy practices that are generally recognized as meeting or exceeding industry or governmental requirements for maintaining the privacy of users. Such information regarding the use of personal data should be prominent and easily accessible by users, and should be updated as the collection and/or use of data changes. Personal information from users should be collected for legitimate uses only. Further, such collection/sharing should occur only after receiving the consent of the users or other legitimate basis specified in applicable law. Additionally, such entities should consider taking any needed steps for safeguarding and securing access to such personal information data and ensuring that others with access to the personal information data adhere to their privacy policies and procedures. Further, such entities may subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations that may serve to impose a higher standard. For instance, in the US, collection of or access to certain health data may be governed by federal and/or state laws, such as the Health Insurance Portability and Accountability Act (HIPAA); whereas health data in other countries may be subject to other regulations and policies and should be handled accordingly.

Despite the foregoing, the present disclosure also contemplates embodiments in which users selectively block the use of, or access to, personal information data. That is, the present disclosure contemplates that hardware and/or software elements may be provided to prevent or block access to such personal information data. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk may be minimized by limiting the collection of data and deleting data once it is no longer needed. In addition, and when applicable, including in certain healthcare-related applications, data de-identification may be used to protect a user's privacy. De-identification may be facilitated, when appropriate, by removing identifiers, controlling the amount or specificity of data stored, controlling how data is stored (e.g., aggregating data across users), and/or other methods such as differential privacy.

Therefore, although the present disclosure broadly covers use of personal information data to implement one or more various disclosed embodiments, the present disclosure also contemplates that the various embodiments may also be implemented without the need for accessing such personal information data. That is, the various embodiments of the present technology are not rendered inoperable due to the lack of all or a portion of such personal information data. For example, content may be selected and delivered to users based on aggregated non-personal information data or a bare minimum amount of personal information, such as the content being handled only on the user's device or other non-personal information available to the content delivery services.

Although specific embodiments have been described, various modifications, alterations, alternative constructions, and equivalents are also encompassed within the scope of the disclosure. Embodiments are not restricted to operation within certain specific data processing environments, but are free to operate within a plurality of data processing environments. Additionally, although embodiments have been described using a particular series of transactions and steps, it should be apparent to those skilled in the art that the scope of the present disclosure is not limited to the described series of transactions and steps. Various features and aspects of the above-described embodiments may be used individually or jointly.

Further, while embodiments have been described using a particular combination of hardware and software, it should be recognized that other combinations of hardware and software are also within the scope of the present disclosure. Embodiments may be implemented only in hardware, or only in software, or using combinations thereof. The various processes described herein may be implemented on the same processor or different processors in any combination. Accordingly, where components or modules are described as being configured to perform certain operations, such configuration may be accomplished, e.g., by designing electronic circuits to perform the operation, by programming programmable electronic circuits (such as microprocessors) to perform the operation, or any combination thereof. Processes may communicate using a variety of techniques, including but not limited to conventional techniques for inter-process communication, and different pairs of processes may use different techniques, or the same pair of processes may use different techniques at different times.

The specification and drawings are, accordingly, to be regarded in an illustrative rather than a restrictive sense. It will, however, be evident that additions, subtractions, deletions, and other modifications and changes may be made thereunto without departing from the broader spirit and scope as set forth in the claims. Thus, although specific disclosure embodiments have been described, these are not intended to be limiting. Various modifications and equivalents are within the scope of the following claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. All methods described herein may be performed in any suitable order unless otherwise indicated herein or otherwise clearly contradicted by context. The use of any and all examples, or exemplary language (e.g., "such as") provided herein, is intended merely to better illuminate embodiments and does not pose a limitation on the scope of the disclosure unless otherwise claimed. No language in the specification should be construed as indicating any non-claimed element as essential to the practice of the disclosure.

Disjunctive language such as the phrase "at least one of X, Y, or Z," unless specifically stated otherwise, is intended to be understood within the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Preferred embodiments of this disclosure are described herein, including the best mode known for carrying out the disclosure. Variations of those preferred embodiments may become apparent to those of ordinary skill in the art upon reading the foregoing description. Those of ordinary skill should be able to employ such variations as appropriate and the disclosure may be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein.

All references, including publications, patent applications, and patents, cited herein are hereby incorporated by reference to the same extent as if each reference were individually and specifically indicated to be incorporated by reference and were set forth in its entirety herein.

In the foregoing specification, aspects of the disclosure are described with reference to specific embodiments thereof, but those skilled in the art will recognize that the disclosure is not limited thereto. Various features and aspects of the above-described disclosure may be used individually or jointly. Further, embodiments may be utilized in any number of environments and applications beyond those described herein without departing from the broader spirit and scope of the specification. The specification and drawings are, accordingly, to be regarded as illustrative rather than restrictive.

What is claimed is:

1. A computer-implemented method, comprising:
    receiving, by a first computing device, a message comprising a description of an event of a first person in an environment from a first user device and via a first transmission protocol;
    detecting, by the first computing device, that the message is an event message;
    transmitting, by the first computing device, the event message to a second computing device in the environment using a second transmission protocol, the second transmission protocol being used based at least in part on detecting that the message is the event message, the first computing device and the second computing device being in operable communication using a local area network; and
    receiving, by the first computing device and using the second transmission protocol, a response from the second computing device indicating that the second computing device has transmitted the event message to a second user device.

2. The computer-implemented method of claim 1, wherein the method further comprises:
    initiating, in response to receiving the event message, a virtual assistant to ask whether the first person wants assistance;
    receiving a message from the virtual assistant comprising a response as to whether the first person wants assistance; and
    transmitting the event message to the second computing device based at least in part on the response as to whether the first person wants assistance.

3. The computer-implemented method of claim 1, wherein the event message further comprises an identity of a user account associated with the first user device, and a location of the first user device in the environment.

4. The computer-implemented method of claim 1, wherein the response from the second computing device comprises a confidence score calculated by the second computing device, and wherein the confidence score describes a probability that a second person is present in proximity to the second user device.

5. The computer-implemented method of claim 1, wherein detecting that the message is the event message comprises detecting an event message identifier.

6. The computer-implemented method of claim 1, wherein the method further comprises:
    detecting the second computing device and a third computing device in the environment,
    wherein transmitting the event message to the second computing device comprises transmitting, to the second computing device and the third computing device, the event message and an identity of the second computing device and the third computing device.

7. The computer-implemented method of claim 1, wherein the method further comprises:
    detecting a fourth computing device based at least in part on an account of a smart home platform, wherein the fourth computing device is outside the environment; and wherein transmitting the event message to the second computing device comprises transmitting, to the second computing device and the fourth computing device, the event message and an identity of the second computing device and an identity of the fourth computing device.

8. A first computing device comprising:
a processor; and
a computer-readable medium including instructions that, when executed by the processor, cause the processor to perform operations comprising:
receiving a message comprising a description of an event of a first person in an environment from a first user device and via a first transmission protocol;
detecting that the message is an event message;
transmitting the event message to a second computing device in the environment using a second transmission protocol, the second transmission protocol being used based at least in part on detecting that the message is the event message, the first computing device and the second computing device being in operable communication using a local area network; and
receiving, using the second transmission protocol, a response from the second computing device indicating that the second computing device has transmitted the event message to a second user device.

9. The computer system of claim 8, wherein the instructions further cause the processor to perform operations comprising:
initiating, in response to receiving the event message, a virtual assistant to ask whether the first person wants assistance; receive a message from the virtual assistant comprising a response as to whether the first person wants assistance; and
receiving a message from the virtual assistant comprising a response as to whether the first person wants assistance; and
transmitting the event message to the second computing device based at least in part on the response as to whether the first person wants assistance.

10. The computer system of claim 9, wherein the event message further comprises an identity of a user account associated with the first user device, and a location of the first user device in the environment.

11. The computer system of claim 9, wherein the response from the second computing device comprises a confidence score calculated by the second computing device, and wherein the confidence score describes a probability that a second person is present in proximity to the second user device.

12. The computer system of claim 9, wherein detecting that the message is the event message comprises detecting an event message identifier.

13. The computer system of claim 9, wherein the instructions that, when executed by the processor, further cause the processor to perform operations comprising:
detecting the second computing device and a third computing device in the environment; and
detecting the second computing device and the third computing device in the environment,
wherein transmitting the event message to the second computing device comprises transmitting, to the second computing device and the third computing device, the event message and an identity of the second computing device and the third computing device.

14. The computer system of claim 9, wherein the instructions that, when executed by the processor, further cause the processor to perform operations comprising:
detecting a fourth computing device based at least in part on an account of a smart home platform, wherein the fourth computing device is outside the environment; and wherein transmitting the event message to the second computing device comprises transmitting, to the second computing device and the fourth computing device, the event message and an identity of the second computing device and an identity of the fourth computing device.

15. A non-transitory computer-readable medium having stored thereon a sequence of instructions that, when executed by a processor, cause the processor to perform operations comprising:
receiving a message comprising a description of an event of a first person in an environment from a first user device and via a first transmission protocol;
detecting that the message is an event message;
transmitting the event message to a second computing device in the environment using a second transmission protocol, the second transmission protocol being used based at least in part on detecting that the message is the event message, a first computing device and the second computing device being in operable communication using a local area network; and
receiving, using the second transmission protocol, a response from the second computing device indicating that the second computing device has transmitted the event message to a second user device.

16. The non-transitory computer-readable medium of claim 15, wherein the instructions further cause the processor to perform operations comprising:
initiating, in response to receiving the event message, a virtual assistant to ask whether the first person wants assistance; receive a message from the virtual assistant comprising a response as to whether the first person wants assistance; and
receiving a message from the virtual assistant comprising a response as to whether the first person wants assistance; and
transmitting the event message to the second computing device based at least in part on the response as to whether the first person wants assistance.

17. The non-transitory computer-readable medium of claim 15, wherein the response from the second computing device comprises a confidence score calculated by the second computing device, and wherein the confidence score describing a probability that a second person is present in proximity to the second user device.

18. The non-transitory computer-readable medium of claim 15, wherein the response from the second computing device comprises a confidence score calculated by the second computing device, and wherein the confidence score describes a probability that a second person is present in proximity to the second user device.

19. The non-transitory computer-readable medium of claim 15, wherein detecting that the message is the event message comprises detecting an event message identifier.

20. The non-transitory computer-readable medium of claim 15, wherein the instructions that, when executed by the processor, further cause the processor to perform operations comprising
detecting the second computing device and a third computing device in the environment; and
detecting the second computing device and the third computing device in the environment,
wherein transmitting the event message to the second computing device comprises transmitting, to the second computing device and the third computing device, the event message and an identity of the second computing device and the third computing device.

\* \* \* \* \*